(12) United States Patent
Enomoto et al.

(10) Patent No.: US 9,327,258 B2
(45) Date of Patent: May 3, 2016

(54) POROUS SILICA-BASED PARTICLES HAVING SMOOTH SURFACE, METHOD FOR PRODUCTION THEREOF AND COSMETIC COMPRISING SUCH PARTICLES

(75) Inventors: Naoyuki Enomoto, Kitakyushu (JP); Yasutaka Miyoshi, Kitakyushu (JP); Tsuneo Kawashima, Kitakyushu (JP); Takumi Miyazaki, Kitakyushu (JP)

(73) Assignee: JGC Catalysts and Chemicals Ltd., Kawasaki-shi (JP)

( * ) Notice: Subject to any disclaimer, the term of this patent is extended or adjusted under 35 U.S.C. 154(b) by 118 days.

(21) Appl. No.: 12/746,007

(22) PCT Filed: Dec. 12, 2007

(86) PCT No.: PCT/JP2007/073980
§ 371 (c)(1),
(2), (4) Date: Jun. 3, 2010

(87) PCT Pub. No.: WO2009/072218
PCT Pub. Date: Jun. 11, 2009

(65) Prior Publication Data
US 2010/0247914 A1    Sep. 30, 2010

(30) Foreign Application Priority Data

Dec. 7, 2007    (JP) .................................. 2007-317754

(51) Int. Cl.
*B32B 1/00* (2006.01)
*B29B 9/16* (2006.01)
*B01J 6/00* (2006.01)
*A61K 8/25* (2006.01)
(Continued)

(52) U.S. Cl.
CPC ................. *B01J 6/001* (2013.01); *A61K 8/025* (2013.01); *A61K 8/0279* (2013.01); *A61K 8/25* (2013.01); *A61Q 1/02* (2013.01); *A61Q 17/04* (2013.01); *A61Q 19/00* (2013.01); *C01B 33/12* (2013.01); *C01B 33/18* (2013.01); *A61K 2800/412* (2013.01); *Y10T 428/2982* (2015.01)

(58) Field of Classification Search
None
See application file for complete search history.

(56) References Cited

U.S. PATENT DOCUMENTS 4,837,011 A * 6/1989 Macchio et al. ................. 424/69
5,028,360 A * 7/1991 Ito et al. ......................... 264/12
(Continued)

FOREIGN PATENT DOCUMENTS

| JP | 61270201 A | 11/1986 |
|---|---|---|
| JP | 62096310 A | 5/1987 |

(Continued)

OTHER PUBLICATIONS

Machine translation of JP 2003-066462.*
(Continued)

*Primary Examiner* — Alexandre Ferre
(74) *Attorney, Agent, or Firm* — The Webb Law Firm

(57) ABSTRACT

Disclosed are porous silica-based particles having high surface smoothness, a method for producing the porous silica-based particles, and a cosmetic comprising the porous silica-based particles. The porous silica-based particles have an average particle diameter of 0.5 to 30 μm and have a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen.

13 Claims, 12 Drawing Sheets

(51) Int. Cl.

| | | |
|---|---|---|
| A61Q 1/02 | (2006.01) | |
| A61Q 17/04 | (2006.01) | |
| A61Q 19/00 | (2006.01) | |
| C01B 33/12 | (2006.01) | |
| C01B 33/18 | (2006.01) | |
| A61K 8/02 | (2006.01) | |

(56) References Cited

U.S. PATENT DOCUMENTS

| | | | | |
|---|---|---|---|---|
| 5,078,801 | A * | 1/1992 | Malik | 134/29 |
| 6,495,257 | B1 * | 12/2002 | Terase et al. | 428/404 |
| 7,976,812 | B2 | 7/2011 | Yamada et al. | |
| 2003/0108580 | A1 * | 6/2003 | Hasenzahl et al. | 424/401 |
| 2005/0047985 | A1 * | 3/2005 | Mori et al. | 423/335 |
| 2008/0160276 | A1 | 7/2008 | Inoue et al. | |

FOREIGN PATENT DOCUMENTS

| | | | |
|---|---|---|---|
| JP | 62230609 | A | 10/1987 |
| JP | 5201830 | A | 8/1993 |
| JP | 826716 | A | 1/1996 |
| JP | 9208215 | A | 8/1997 |
| JP | 11147711 | A | 6/1999 |
| JP | 11292529 | A | 10/1999 |
| JP | 2000319012 | A | 11/2000 |
| JP | 2003066462 | A | 3/2003 |
| JP | 200554130 | A | 3/2005 |
| JP | 200554131 | A | 3/2005 |
| JP | 2005060283 | A | 3/2005 |
| JP | 2006176343 | A | 7/2006 |
| JP | 2006248971 | A | 9/2006 |
| WO | 2007/122930 | A1 | 11/2007 |

OTHER PUBLICATIONS

Hu et al. (Influence of the Zeta Potential on the Dispersibility and Purification of Single-Walled Carbon Nanotubes, J. Phys. Chem. B. 2005, 109, 11520-11524).*

Machine translation Nobuaki et al. (Jap. Pat. No. 2003-066462). (2003).*

Kani, Toshiyuki, "Optical and Physical Property Characterization and Control of Cosmetics Fine Powder Raw Material", Tokyo University of Agriculture and Technology Thesis (2007), pp. 45-64, Koganei, Tokyo, JP.

Database WPI, Week 200780, Thomson Scientific, London, GB; AN 2007-872507, XP002752818.

Database WPI, Week 200378, Thomson Scientific, London, GB; AN 2003-836393, XP002752819.

Chen, Hongmin, et al., "Rapid evaporation-induced synthesis of monodisperse budded silica spheres", Journal of Colloid and Interface Science, Academic Press, New York, NY, US, vol. 316, No. 2, Nov. 5, 2007, pp. 211-215, XP022328610.

* cited by examiner

POROUS SILICA-BASED PARTICLES HAVING SMOOTH SURFACE, METHOD FOR PRODUCTION THEREOF AND COSMETIC COMPRISING SUCH PARTICLES

TECHNICAL FIELD

The present invention relates to porous silica-based particles having a high surface smoothness, a method for producing the porous silica-based particles, and a cosmetic comprising the porous silica-based particles.

BACKGROUND ART

A number of methods are known for producing porous silica-based particles, and representative examples thereof include (1) a method in which silica sol or the like is spray-dried with use of a spray dryer, and (2) a method in which silica-based particles are produced by an emulsion method.

For example, Patent Document 1 discloses a spray-drying method in which porous silica-based particles having an average particle diameter of 1 to 20 μm are produced by spray-drying a colloidal liquid containing primary particles having an average particle diameter of not more than 250 nm (i.e., fine silica-based particles) with use of a spray dryer.

Patent Document 2 discloses an emulsion method in which water glass (i.e., sodium silicate) is added into an organic solvent containing a surfactant such as an ester of sorbitan fatty acid to give an emulsion which is then neutralized to produce porous silica-based particles having an average particle diameter of 0.1 to 5,000 μm.

These patent documents, however, neither describe nor suggest the method for producing porous silica-based particles having a smooth surface as defined in the present invention.

Further, it is generally known that spherical porous silica-based particles and the like are blended as a feeling-improving agent into a cosmetic.

For example, Patent Document 3 discloses a method for producing a solid cosmetic such as a powdery foundation having high slippage and smooth feeling of use by blending porous silica-based particles into a cosmetic.

Patent Document 4 discloses that blending of spherical porous silica-based particles having a refractive index of 1.3 to 1.8 into a cosmetic improves spreadability of the cosmetic in use and uniformity of a cosmetic film.

These patent documents, however, neither describe nor suggest the cosmetic comprising porous silica-based particles having a smooth surface as defined in the present invention.

On the other hand, Non-patent Document 1 discloses that foreign matters such as small particles with a nanosize attached to the surface of commercially available silica-based particles are removed by an ultrasonic cleaning method to improve the surface smoothness of the particles. Non-patent Document 1 further describes that the silica-based particles thus obtained are suitable for applications of cosmetics such as foundations.

Even when the method using the ultrasonic cleaning is applied, however, foreign matters such as small particles with a nanosize will not be completely removed from the surface of the silica-based particles. Further, the porous silica-based particles per se are likely to be collapsed by the impact of ultrasonic waves, and it becomes difficult to obtain a large number of the particles with a high sphericity.

Patent Document 1: Japanese Patent Application Publication No. 270201/1986

Patent Document 2: Japanese Patent Application Publication No. 230609/1987

Patent Document 3: Japanese Patent Application Publication No. 60283/2005

Patent Document 4: Japanese Patent Application Publication No. 248971/2006

Non-patent Document 1: Toshiyuki KANI, Tokyo University of Agriculture and Technology 2007, Page 45-64

SUMMARY OF THE INVENTION

The present inventors have made extensive and intensive studies with a view to solving the above problems and, as a result, have found that, when a dried powder of porous silica-based particles produced by the spray-drying method, the emulsion method or the like is put into water followed by stirring under given conditions, foreign matters such as small particles with a nanosize can be removed from the surface of the particles, and that porous silica-based particles having a desired average particle diameter can be obtained by further subjecting the treated particles to a wet classification device or devices. The finding has led to the completion of the present invention, An object of the present invention is to provide porous silica-based particles having a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen, and a method for producing the porous silica-based particles. Another object of the present invention is to provide a cosmetic comprising the porous silica-based particles having the above properties as a feeling-improving agent (sometimes herein referred to as "a feeling-improving material").

The porous silica-based particles according to the present invention have an average particle diameter of 0.5 to 30 μm and have a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen.

For the porous silica-based particles, it is preferable that, when a surface roughness value of the particle is given by measuring a difference between a circumscribed circle and an inscribed circle at a boundary of the particle observed from a photograph of a cross-section thereof taken by a transmission electron microscope (TEM) with a magnifying power of 100,000, the particles have a surface roughness value of not more than 20 nm.

Further, it is preferable that the porous silica-based particles have a non-sphericity of not more than 5%.

Further, it is preferable that the porous silica-based particles have an oil absorption rate in a range of 20 to 300 ml/100 g.

Further, it is preferable that the porous silica-based particles have a pore volume in a range of 0.05 to 3.0 ml/g.

Further, it is preferable that the porous silica-based particles have a coefficient of variation (CV value) in a range of 5 to 50%.

Further, it is preferable that the porous silica-based particles have a silica purity ($SiO_2$ content) of not less than 96% by weight.

The present invention further provides a method for producing porous silica-based particles having an average particle diameter of 0.5 to 30 μm and having a surface smoothness of a level to such an extent that, when the entire surface of the particles is observed from a photograph thereof taken by a scanning electron microscope (SEM) with a magnifying power of 10,000, a foreign matter attached to the surface thereof can be hardly seen, which comprises the steps of:

(a) spray-drying a dispersion of fine silica-based particles, or a mixture of the above dispersion of the fine silica-based particles and an aqueous solution of silicic acid with use of a spray dryer, to obtain a dried powder of porous silica-based particles having diameters ranging primarily from 0.1 to 50 μm;

(b) putting the dried powder of the porous silica-based particles obtained in the step (a) into water and then stirring a slurry of the mixture under pH conditions on which the zeta potential of the porous silica-based particles contained in the water comes to in a range of −15 to −70 mV, to obtain a dispersion of porous silica-based particles with a foreign matter attached to the surface thereof having been removed therefrom;

(c) subjecting the dispersion obtained in the step (b) to a wet classification device at which a supernatant containing at least porous silica-based particles having diameters of less than 0.5 μm is separated and removed, to obtain a dispersion containing porous silica-based particles having diameters ranging primarily from 0.5 to 50 μm;

(d) subjecting the dispersion obtained in the step (c) to a wet classification device at which a sediment or precipitate containing at least porous silica-based particles having diameters of more than 30 μm is separated and removed, to obtain a dispersion containing porous silica-based particles having diameters ranging primarily from 0.5 to 30 μm;

(e) filtering the dispersion obtained in the step (d) to separate solid materials contained therein, to obtain a cake-like substance of porous silica-based particles; and (f) drying the cake-like substance obtained in the step (e) and then crushing or breaking up a group of thus obtained particles, to obtain a dried powder of porous silica-based particles having an average particle diameter of 0.5 to 30 μm.

In the step (b) above, it is preferable that the pH of the slurry containing the dried powder of the porous silica-based particles is in a range of 5 to 10.

Further, In the step (b) above, it is preferable that the zeta potential of the porous silica-based particles contained in the water is in a range of −20 to −60 mV.

Further, it is preferable that the stirring operation in the step (b) above is performed for at least three minutes at a stirring speed of 10 to 5,000 rpm.

Further, it is preferable that the wet classification device used in the step (c) above is a centrifugal separator, a liquid cyclone, or an elutriator (a natural sedimentation device).

Further, it is preferable that the wet classification device used in the step (d) above is a centrifugal separator, a liquid cyclone, or an elutriator (a natural sedimentation device).

Further, it is preferable that the drying operation in the step (f) above is performed for 1 to 24 hours at a temperature of room temperature to 200° C.

Further, it is preferable that the dried powder of the porous silica-based particles obtained in the step (f) above is further calcined at a temperature of 200 to 800° C. for 1 to 24 hours.

The present invention further provides a cosmetic comprising the porous silica-based particles having the surface smoothness as described above.

Further, it is preferable that the cosmetic is a makeup cosmetic, a skin care cosmetic, or a sunscreen cosmetic.

The porous silica-based particles according to the present invention are spherical silica-based particles which have, despite its porous nature, an average particle diameter of 0.5 to 30 μm and also a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen. The porous silica-based particles have the following properties:

(1) The surface roughness value of the particles defined in the present invention is not more than 20 nm.

(2) The non-sphericity of the particles is not more than 5% (that is, the sphericity of the particles is more than 95%).

(3) The oil absorption rate of the particles is in a range of 20 to 300 ml/100 g.

(4) The pore volume of the particles is in a range of 0.05 to 3.0 ml/g.

(5) The coefficient of variation (CV value) of the particles is in a range of 5 to 50%.

(6) The silica purity ($SiO_2$ content) of the particles is not less than 96% by weight.

In the method for producing porous silica-based particles according to the present invention, the porous silica-based particles having the above properties can be produced in a simple and easy manner without the need to use any special equipment (for example, an ultrasonic cleaning device).

The porous silica-based particles have the high sphericity and further have a sharp particle size distribution. Accordingly, as the frictional resistance among the particles becomes low, the particles are suitable for use in blending into cosmetics. That is, when the cosmetics blended with the porous silica-based particles as a feeling-improving material are used, most of the panelists for a sensory test thereof will have good feelings of smoothness, moistness, rolling effect, even spreadability, adhesiveness, and sustainability of the rolling effect on or onto the skin, all of which are main feeling properties requisite for the feeling-improving material to be blended in cosmetics, and, thus, a balanced effect unattainable by the conventional silica-based particles can be imparted to the cosmetics.

As the silica-based particles according to the present invention are porous, the cosmetics comprising such porous silica-based particles can be satisfactorily expected to offer, for example, the effect of removing sebum. Further, a grating feeling which is inherent in silica-based particles can be reduced, and, thus, it is expected that a range of application to the cosmetics as the feeling-improving material may be significantly expanded.

BEST MODE FOR CARRYING OUT THE INVENTION

The porous silica-based particles according to the present invention and the method for producing such particles are described below in more detail.

[Porous Silica-Based Particles]

The porous silica-based particles according to the present invention have an average particle diameter of 0.5 to 30 µm, preferably 2 to 10 µm, and have a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen.

When the particles having an average particle diameter of less than 0.5 µm are used, upon applying a powder of such particles onto the skin, most of the panelists as described above will feel a lack of rolling effect as the spherical particles and at the same time, a poor even spreadability. On the other hand, when the particles having an average particle diameter of more than 30 µm are used, upon applying a powder of such particles onto the skin, most of the panelists as described above will feel to be harsh and grating.

Figure 4:
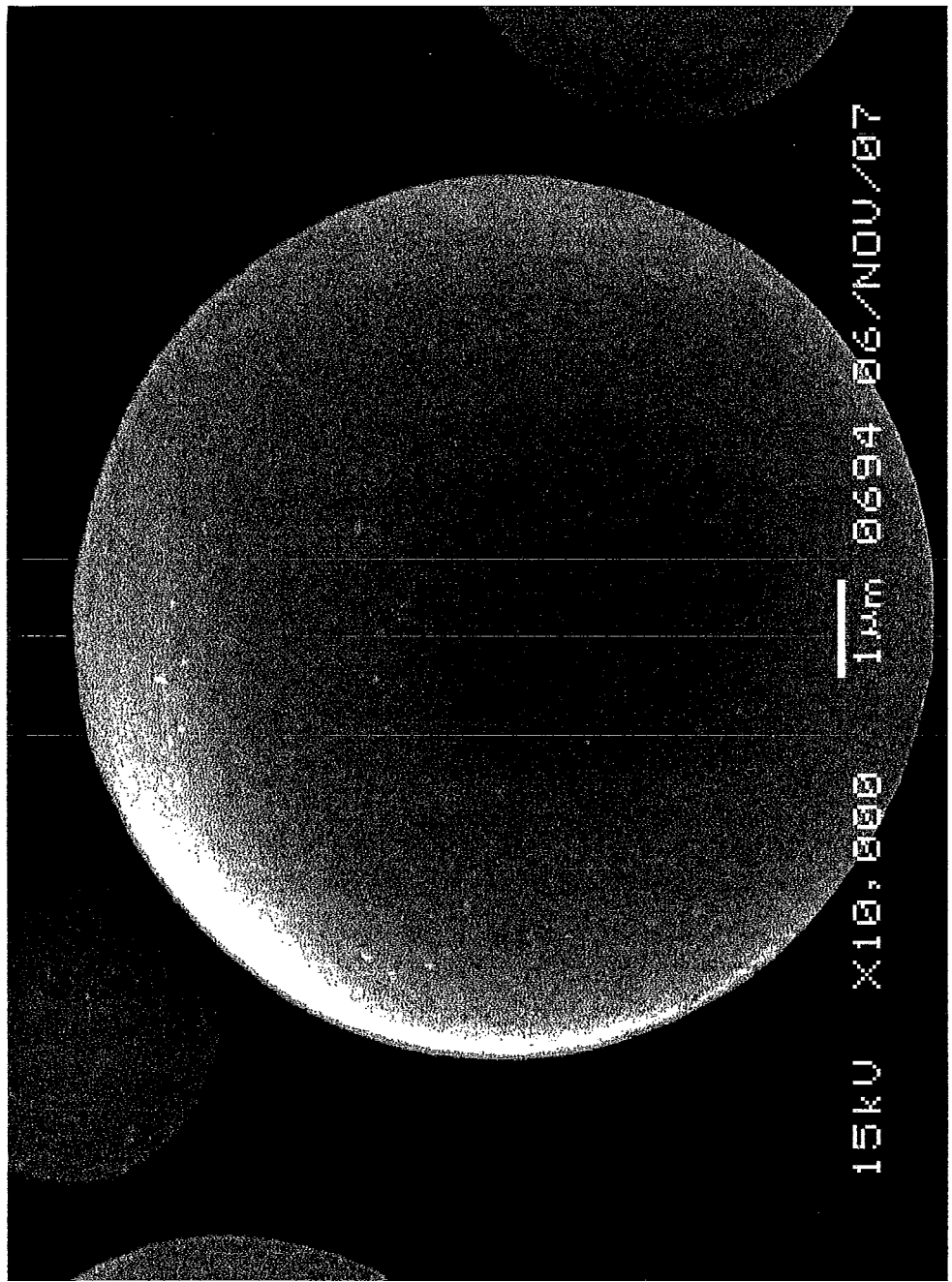
FIG. 4 is a photograph of porous silica-based particles, which were obtained in a calcination step in Example 1 (i.e., the particles produced by calcining a dried powder of porous silica-based particles classified under a wet condition), taken by a scanning electron microscope (SEM) with a magnifying power of 10,000.

In the present invention, as shown in FIG. 4, the expression "a surface smoothness of a level to such an extent that a foreign matter attached to the surface thereof can be hardly seen" refers to such a state that, when the entire surface of the porous silica-based particle is observed from a photograph thereof taken by a scanning electron microscope (SEM) with a magnifying power of 10,000, a foreign matter attached to the surface thereof can be hardly seen. In this case, even though small particles with a nanosize (observed as white dots in FIG. 4) and the like are attached to a part of the surface of the porous silica-based particles, the above requirement is satisfied when the number of the small particles (including particles observed as white dots on the photograph) which are present per µm$^2$ of the plane surface as determined using an SEM photograph is 5 or less.

Figure 11:
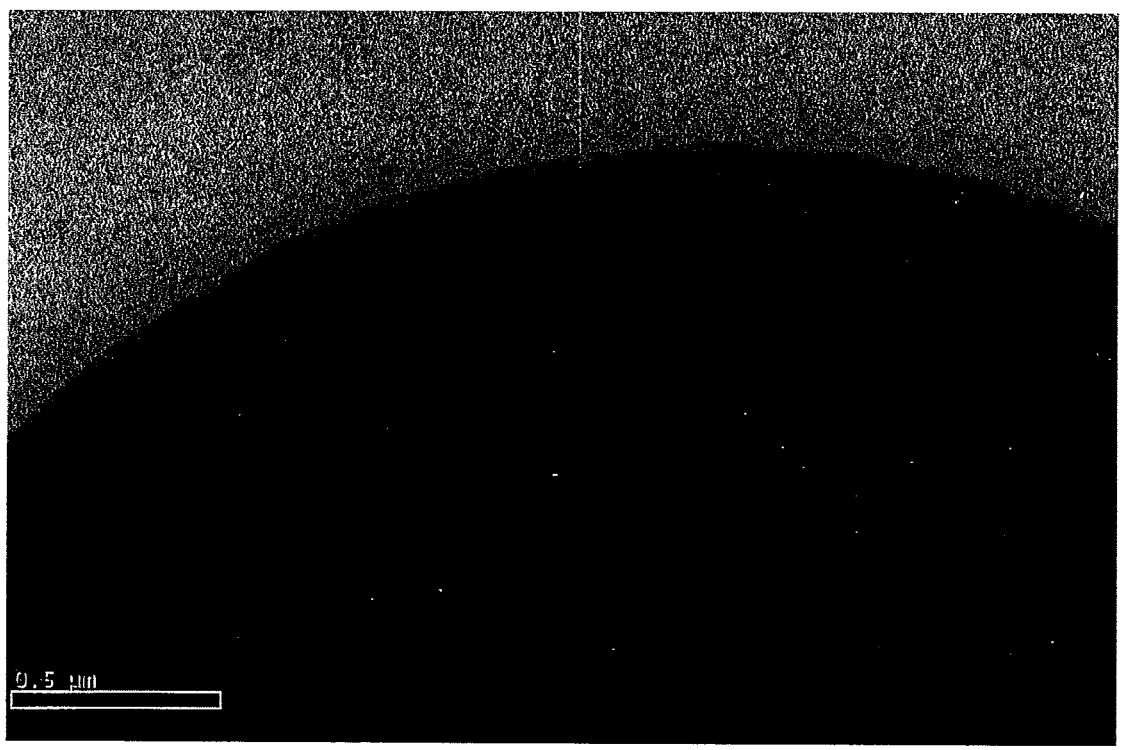
FIG. 11 is a photograph of cross-section of a porous silica-based particle, which was obtained in a calcination step in Example 1 (i.e., the particle produced by calcining a dried powder of porous silica-based particles classified under a wet condition), taken by a transmission electron microscope (TEM) with a magnifying power of 100,000.

Further, the expression sometimes refers to such a state that, as shown in FIG. 11, when a surface roughness value of the porous silica-based particle is given by measuring a difference between a circumscribed circle and an inscribed circle at a boundary of the particle observed from a photograph of a cross-section thereof taken by a transmission electron microscope (TEM) with a magnifying power of 100,000, the particles have a surface roughness value of not more than 20 nm.

The surface roughness value is not more than 20 nm, preferably not more than 15 nm, still preferably not more than 10 nm, on the average of the particles as measured by the above method. When the surface roughness value exceeds 20 nm, the frictional resistance among particles in rolling of the particles is increased.

In the porous silica-based particles according to the present invention, the surface smoothness is not less than 70%, preferably not less than 80%, still more preferably not less than 90%, as determined by visually counting, using an SEM photograph, the number of particles for which a foreign matter is seen (that is, the number of particles for which the number of the small particles present per µm$^2$ of the plane surface on the porous silica-based particle is 6 or more) on samples of more than 100 particles randomly picked out, and then by calculating the surface smoothness based on the counted number by the following equation:

Surface smoothness (%)=$(T-P)/T \times 100$, wherein "T" represents the total number of the particles observed; and "P" represents the counted number of the particles for which the foreign matters as described above have been seen.

When the surface smoothness is less than 70%, the frictional resistance among the particles in rolling of the particles becomes high. Therefore, upon applying a powder of such particles onto the skin, most of the panelists as described above will not have good feelings of smoothness, moistness, rolling effect, even spreadability, adhesiveness, sustainability of the rolling effect, as required for the feeling-improving material, and will feel to be grating, the feeling of which is not good but is inherent in the silica-based particles.

The non-sphericity of the porous silica-based particles is not more than 5%, preferably not more than 2%, still more preferably not more than 1%. When the non-sphericity of the porous silica-based particles is more than 5%, upon applying a powder of such particles onto the skin, most of the panelists as described above will not have good feelings of smoothness, moistness, rolling effect, even spreadability, adhesiveness, sustainability of the rolling effect, as required for the feeling-improving material, and will feel to be grating, the feeling of which is not good but is inherent in the silica-based particles.

The term "non-sphericity" as used herein refers to the proportion of particles which are not spherical or not near-spherical, in other words, the proportion of particles which have been bonded to each other or one another or collapsed for some reasons.

The oil absorption rate of the porous silica-based particles is 20 to 300 ml/100 g, preferably 60 to 230 ml/100 g. When the oil absorption rate is less than 20 ml/100 g, as the effect of removing sebum becomes low, the particles having such oil absorption rate are not necessarily practical as an ingredient of the cosmetic. On the other hand, when the oil absorption rate is more than 300 ml/100 g, as the effect of removing sebum becomes high, the skin may be irritated, and further, as the porosity of the particle per se becomes high, the compressive strength of the particle is lowered. Therefore, the particle is likely to be collapsed upon applying a powder of such particles onto the skin, resulting in a significantly deteriorated sustainability of the rolling effect.

The pore volume of the porous silica-based particles is 0.05 to 3.0 ml/g, preferably 0.3 to 1.9 ml/g. When the pore volume is less than 0.05 ml/g, as the porosity of the particle per se becomes low, the oil absorption into pores existing in the particle is lowered. Further, in this case, as the particle per se is relatively heavy, upon applying a powder of such particles onto the skin, most of the panelists as described above will not have good feelings of smoothness, rolling effect, even spreadability and sustainability of the rolling effect. On the other hand, when the pore volume is more than 3.0 ml/g, as the porosity of the particle per se becomes high, the compressive strength of the particle is lowered. Therefore, the particle is likely to be collapsed upon applying a powder of such particles onto the skin, resulting in a significantly deteriorated sustainability of the rolling effect.

The coefficient of variation (CV value) of the porous silica-based particles is 5 to 50%, preferably 10 to 30%. When the coefficient of variation is more than 50%, such particles will necessarily make random rolling, and consequently, the feeling properties requisite for the feeling-improving material as described above will not be satisfied. In the present invention, although the particles having a coefficient of variation of less than 5% can be used, the production of such porous silica-based particles requires a high cost, and any particular effect which is worth the cost may not be expected. For the above reason, the lower limit of the coefficient of variation is set at 5%.

Further, the purity ($SiO_2$ content) of the porous silica-based particles is not less than 96% by weight, preferably not less than 99% by weight. When the purity is less than 96% by weight, the purity required of silicic anhydride in the Standards of Cosmetic Ingredients will not be satisfied and, consequently, it is difficult to use the porous silica-based particles as a cosmetic ingredient. When the porous silica-based particles are produced by a spray-drying method which will be described later, there is no need to use a starting feed material containing an organic component. Accordingly, the porous silica-based particles do not contain carbon or carbonaceous materials originated from the organic component. Even when a starting feed material containing an organic component (for example, an organic solvent) is used, the carbon content (C content) of the porous silica-based particles is less than 1,000 ppm by weight, preferably less than 100 ppm by weight. When the carbon content is not less than 1,000 ppm by weight, coloring or an unusual odor considered as deriving from a deterioration in the organic component sometimes occurs and, consequently, the usefulness of the porous silica-based particles as a cosmetic ingredient is lowered.

[Method for Producing Porous Silica-Based Particles]

The method for producing porous silica-based particles according to the present invention is described below in detail. However, it should be noted that the porous silica-based particles according to the present invention are not limited to those produced by the method.

The present invention provides a method for producing porous silica-based particles having an average particle diameter of 0.5 to 30 μm and having a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen, which comprises the steps of:

(a) spray-drying a dispersion of fine silica-based particles, or a mixture of the above dispersion of the fine silica-based particles and an aqueous solution of silicic acid with use of a spray dryer, to obtain a dried powder of porous silica-based particles having diameters ranging primarily from 0.1 to 50 μm;

(b) putting the dried powder of the porous silica-based particles obtained in the step (a) into water and then stirring a slurry of the mixture under pH conditions on which the zeta potential of the porous silica-based particles contained in the water comes to in a range of −15 to −70 mV, to obtain a dispersion of porous silica-based particles with a foreign matter attached to the surface thereof having been removed therefrom;

(c) subjecting the dispersion obtained in the step (b) to a wet classification device at which a supernatant containing at least porous silica-based particles having diameters of less than 0.5 μm is separated and removed, to obtain a dispersion containing porous silica-based particles having diameters ranging primarily from 0.5 to 50 μm;

(d) subjecting the dispersion obtained in the step (c) to a wet classification device at which a sediment or precipitate containing at least porous silica-based particles having diameters of more than 30 μm is separated and removed, to obtain a dispersion containing porous silica-based particles having diameters ranging primarily from 0.5 to 30 μm;

(e) filtering the dispersion obtained in the step (d) to separate solid materials contained therein, to obtain a cake-like substance of porous silica-based particles; and (f) drying the cake-like substance obtained in the step (e) and then crushing or breaking up a group of thus obtained particles, to obtain a dried powder of porous silica-based particles having an average particle diameter of 0.5 to 30 μm.

Next, each of the steps will be described.

Step (a)

In this step, as described above, a dispersion of fine silica-based particles, or a mixture of the above dispersion of the fine silica-based particles and an aqueous solution of silicic acid is subjected to a spray dryer at which spray-drying is performed to produce a dried powder of porous silica-based particles having diameters ranging from 0.1 to 50 μm.

The dispersion of fine silica-based particles may be a commercially available product produced by a conventional method. In the present invention, however, the use of a silica sol in which spherical or non-spherical fine silica-based particles having an average particle diameter of 0.005 to 0.5 μm, preferably 0.005 to 0.1 μm (sometimes herein referred to as "fine silica-based particles") are dispersed in water, is preferred.

In the present invention, fine silica-based particles having an average particle diameter of less than 0.005 μm can be used satisfactorily. However, it is difficult to measure the average particle diameter of less than 0.005 μm by use of a measuring method which will be described later. For this reason, the lower limit of the average particle diameter is set at 0.005 μm. When the average particle diameter is more than 0.5 μm, the binding capability among the fine silica-based particles spray-dried is lowered and, consequently, the compressive strength of thus obtained silica-based particles is lowered.

Examples of such dispersion of fine silica-based particles include a silica sol containing fine silica-based particles having an average particle diameter of about 0.005 μm (Cataloid™ SI-550, manufactured by JGC Catalysts and Chemicals Ltd.), a silica sol containing fine silica-based particles having an average particle diameter of about 0.015 μm (Cataloid™ S-20L, manufactured by JGC Catalysts and Chemicals Ltd.), and a dispersion containing fumed silica having an average particle diameter of about 0.012 μm (AEROSIL™ 200, manufactured by NIPPON AEROSIL CO., LTD.). The dispersion is preferably an aqueous dispersion. The dispersion may, if necessary, contain an alcohol such as ethanol, propanol, or butanol.

Further, the aqueous solution of silicic acid may be one prepared by treating an aqueous solution of a silicate such as an alkali metal silicate or a silicate of an organic base with a cation exchange resin to dealkalize from the silicate (for example, to remove sodium ions). Examples of such silicates include alkali metal silicates such as sodium silicate (water glass) and potassium silicate and silicates of organic bases such as quaternary ammonium silicate.

Among them, an aqueous solution of silicic acid that has a pH value of 2 to 6, preferably 2 to 3, and contains a silicon compound in a range of 0.5 to 10% by weight, preferably 3 to 4% by weight, in terms of $SiO_2$, is preferred. When the pH value is less than 2, the treatment time necessary for cation exchange is very long, and the cost effectiveness is low. On the other hand, when the pH value is more than 6, the degree of dealkalization from the silicate becomes low, and consequently, the stability of the prepared aqueous solution of silicic acid is lowered. When the content of silicon compound is less than 0.5% by weight, the production of the fine silica-based particles in a cost-effective manner becomes difficult. On the other hand, when the content of silicon compound is more than 10% by weight, the stability of the aqueous solution of silicic acid is lowered.

The aqueous solution of silicic acid having the above properties is preferably one prepared by diluting water glass (sodium silicate) with water and treating the diluted water glass with a cation exchange resin to remove alkali component (e.g., sodium ions) from the water glass In the present invention, a mixture of the dispersion of fine silica-based particles and the aqueous solution of silicic acid can be used satisfactorily.

In order to prepare porous silica-based particles having a number of pores or voids, the use of only the dispersion of fine silica-based particles or a material containing at least the dispersion of fine silica-based particles is preferred. However, the silicon compound contained in the aqueous solution of silicic acid functions as a binder component among the fine silica-based particles. Accordingly, when the production of porous silica-based particles having high compressive strength is required, mixing an appropriate amount of the aqueous solution of silicic acid into the dispersion of fine silica-based particles is preferred. However, the use of only the aqueous solution of silicic acid is not preferred because the porosity of the formed silica-based particles is disadvantageously lowered.

Spray-drying in this step can be performed by a conventional method using a commercially available spray dryer (for example, a disk rotation type spray dryer or a nozzle type spray dryer).

That is, the spray-drying is performed by spraying the dispersion of fine silica-based particles, or a silica component-containing dispersion of a mixture comprising the dispersion of the fine silica-based particles and the aqueous solution of silicic acid (hereinafter referred to simply as "dispersion"), for example, at a rate of 1 to 3 liters/min into a hot air stream. In this case, as for the temperature of the hot air, the temperature at the inlet is 70 to 400° C., preferably 100 to 300° C., and the temperature at the outlet is preferably 40 to 60° C. When the temperature at the inlet is below 70° C., the level of drying of the silica-based particles sprayed (which are obtainable from the solid materials contained in the dispersion) is unsatisfactory. On the other hand, when the temperature at the inlet is above 400° C., the shape of the silica-based particles sprayed is disadvantageously distorted during spray-drying. When the temperature at the outlet is below 40° C., as the level of drying of the silica-based particles sprayed becomes low, the silica-based particles and the like splayed will be deposited on the wall inside the apparatus of the splay dryer.

The dispersion is previously adjusted to a solid content of 1 to 50% by weight, preferably 5 to 30% by weight, and then is preferably subjected to a spray dryer for spray-drying. When the solid content is less than 1% by weight, the cost effectiveness is lowered. On the other hand, when the solid content is more than 50% by weight, the viscosity of the slurry is increased and the shape of the spray-dried product is distorted.

When the dispersion containing the aqueous solution of silicic acid is subjected to a spray dryer for spray-drying, the silicon compound contained in the aqueous solution of silicic acid is dehydrated and polycondensed, and consequently is converted to a silica component. Accordingly, in the porous silica-based particles thus obtained, the silicon compound contained in the aqueous solution of silicic acid is present as a dehydrated and polycondensed product.

The porous silica-based particles thus obtained have diameters of about 0.1 to 50 μm.

Figure 2:
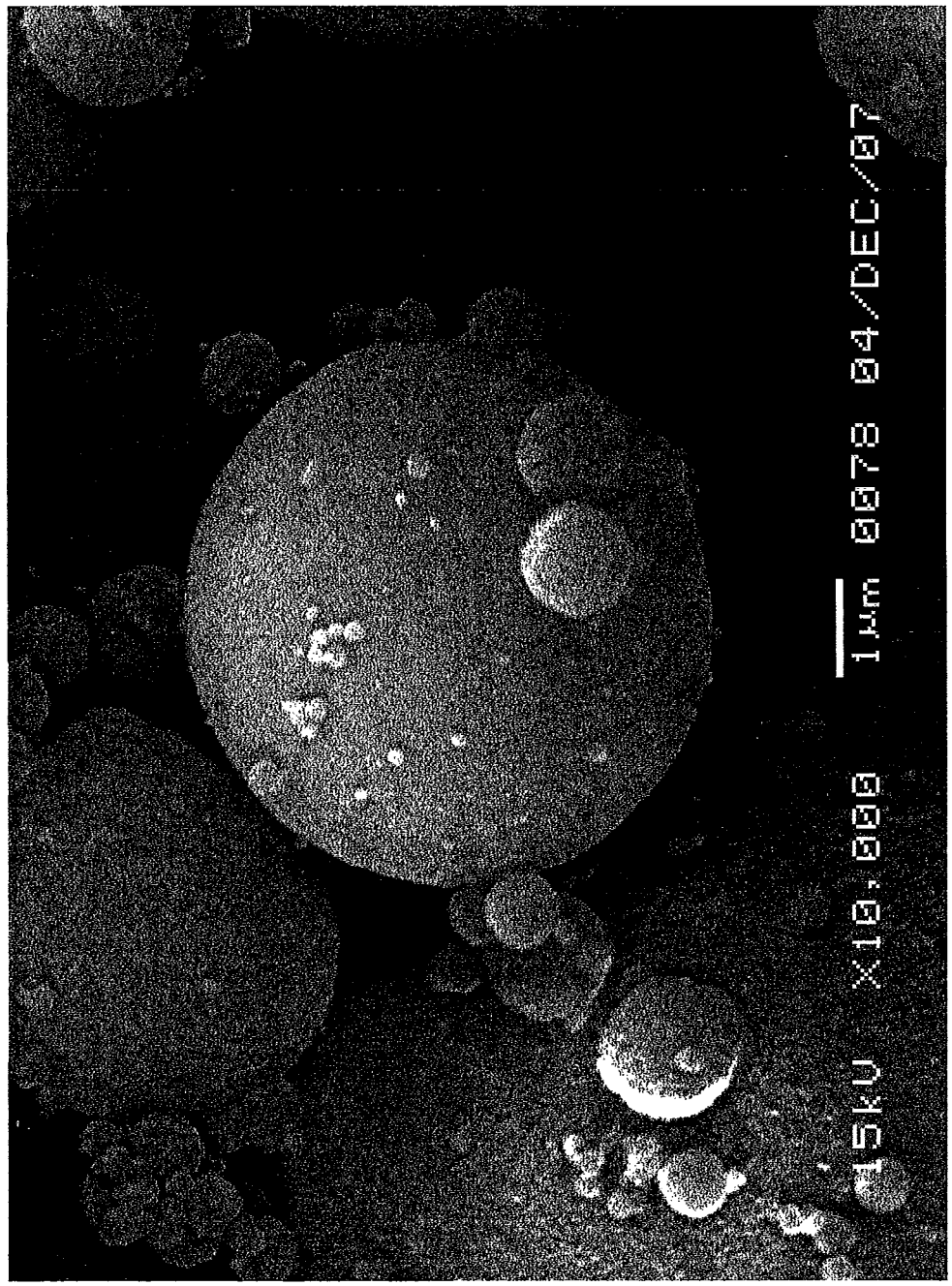
FIG. 2 is a photograph of porous silica-based particles, which were obtained in step (a) (that is, a spray-drying step) in Example 1, taken by a scanning electron microscope (SEM) with a magnifying power of 10,000.

The porous silica-based particles produced by the spray-drying are generally in a spherical or substantially spherical form. However, small particles having diameters of less than about 1 μm, in particular small particles with a nanosize and the like produced in the step of spray-drying are attached to the surface of the porous silica-based particles as the splay-dried product. That is, as shown in FIG. 2, when the entire surface of the porous silica-based particles is taken by a scanning electron microscope (SEM) with a magnifying power of 10,000, the small particles and the like are observed as a foreign matter attached to the surface of the porous silica-based particles. The attachment of the small particles and the like onto the surface of the porous silica-based particles is considered attributable to electrostatic force which acts on between the particles.

Step (b)

In this step, the dried powder of the porous silica-based particles obtained in the step (a) is put into water, and a slurry of the mixture is stirred under pH conditions on which the zeta potential of the porous silica-based particles contained in the water comes to in a range of −15 to −70 mV, to obtain a dispersion of porous silica-based particles with a foreign matter attached to the surface of the particles having been removed therefrom.

It is considered that, when the dried powder of the porous silica-based particles obtained in the step (a) is dispersed in water by stirring, the electrostatic force which acts on between the porous silica-based particle and the small particles attached to the surface of the porous silica-based particle disappears, and, instead, silanol groups present on the surface of the porous silica-based particle are dissociated, and an electric double layer is formed on the surface of the porous silica-based particle, which develops electric repulsive force among the particles to allow the small particles to be separated from the surface of the porous silica-based particles.

When the zeta potential of the porous silica-based particles is low (as an absolute value of the negative potential), the repulsive force by the electric double layer does not satisfactorily function, and therefore, the zeta potential of the particle is preferably in a range of −15 to −70 mV, preferably −20 to −60 mV, more preferably −25 to −55 mV.

Even when the zeta potential is more than −15 mV (e.g., −10 mV), in some cases, the small particles are temporarily separated from the surface of the porous silica-based particles by the mechanical stirring operation. However, as the particles per se are unstable, the small particles are disadvantageously attached again to the surface of the porous silica-based particles with the elapse of time. The small particles re-attached to the surface of the porous silica-based particles, even when subjected to a subsequent wet classification step, will not be removed from the surface of the porous silica-based particles without difficulties. On the other hand, the particles with a zeta potential being less than −70 mV (e.g., −75 mV) can be used. However, the porous silica-based particles having a zeta potential of less than −70 mV will not be prepared, although a zeta potential close to the above figure may be obtained by increasing the amount of the alkali added in the slurry. Whilst, the silica-based particles having a zeta potential of less than −70 mV may be obtainable by incorporation of other metal components into the particles. However, not only the cost for the production thereof is increased, but also the particles obtainable therefrom may not have a silica purity ($SiO_2$ content) of not less than 96% by weight, the purity of which is generally required for silica ingredients to be blended in cosmetics.

In order to impart the zeta potential within the above range to the porous silica-based particles, the pH value in the slurry is brought to 5 to 10, preferably 7 to 9. When the pH value is less than 5, as the amount of the silanol group dissociated from the surface of the particle is not so much, the zeta potential may not be maintained in a satisfactory value. On the other hand, when the pH value is more than 10, the surface of the porous silica-based particles begins to be dissolved, and the silanol group present on the surface of the particle and the silanol group present on the surface of the small particles disadvantageously may cause a reaction of polycondensation to adhere the particles to one another. Further, in some cases, the desired silica purity ($SiO_2$ content) may not be maintained.

Pure water such as an ion-exchange water or a distilled water can be used as the water in which the porous silica-based particles are to be dispersed. However, in order to enhance the zeta potential (that is, to increase an absolute value of the negative potential), the use of pure water with addition of an appropriate amount of alkali such as ammonia or aqueous ammonia is preferred. The pH value of the dispersion prepared by putting and dispersing the porous silica-based particles in pure water varies also depending upon the properties of the particles, but is in many cases 3 to 8. In this case, the pH value of the dispersion containing porous silica-based particles prepared using a dispersion of the fine silica-based particles mixed with the aqueous solution of silicic acid is likely to be on the acid side.

It is desired that the stirring treatment be performed at a stirring speed of 10 to 5,000 rpm, preferably 100 to 1,000 rpm, for three minutes or longer, preferably 0.5 to 24 hours.

When the stirring speed is less than 10 rpm, the small particles and other attached foreign matters may not be removed from the surface of the porous silica-based particles easily. On the other hand, when the stirring speed is more than 5,000 rpm, the particles contained in the slurry will collide with one another and, consequently, some particles may be collapsed. When the stirring time is less than 3 minutes, the small particles and other attached foreign matters may not be removed from the surface of the porous silica-based particles easily. However, stirring for more than 24 hours is not beneficial because removable foreign matters attached to the porous silica-based particles can be removed from the surface of the particles by stirring for about 24 hours.

Step (c)

In this step, a dispersion containing porous silica-based particles having diameters ranging primarily from 0.5 to 50 μm is prepared by subjecting the dispersion obtained in the step (b) to a wet classification device to separate and remove a supernatant containing at least porous silica-based particles having diameters of less than 0.5 μm.

A commercially available conventional device can be used as the wet classification device, and examples thereof include centrifugal separators, liquid cyclones, or elutriators (e.g., natural sedimentation devices). Among them, a centrifugal separator or a liquid cyclone is preferred for the preparation of the dispersion on a commercial scale.

The operation of the wet classification device varies also depending, for example, upon the desired average particle diameter of porous silica-based particles to be collected as the classified product. However, the wet classification device is preferably operated at a centrifugal force of 1 to 10,000 G, preferably 10 to 1,000 G, for 1 to 200 minutes, preferably 2 to 30 minutes.

The reason why, in this step, the supernatant liquid containing porous silica-based particles having diameters of less than 0.5 μm is separated and removed is that for obtaining the porous silica-based particles having an average particle diameter of not less than 0.5 μm. When the average particle diameter of the porous silica-based particles is less than 0.5 μm, upon applying a powder of such particles onto the skin, most of the panelists as described above will feel a lack of rolling effect as the spherical powder and, at the same time, a poor even spreadability.

Step (d)

In this step, a dispersion containing porous silica-based particles having diameters ranging primarily from 0.5 to 30 μm is prepared by subjecting the dispersion obtained in the step (c) to a wet classification device to separate and remove a sediment or precipitate containing at least porous silica-based particles having diameters of more than 30 μm.

As with the step (c), examples of the wet classification devices include centrifugal separators, liquid cyclones, or elutriators (e.g., natural sedimentation devices). Among them, the use of a centrifugal separator or a liquid cyclone is preferred.

The operation of the wet classification device varies also depending, for example, upon the desired average particle diameter of porous silica-based particles to be collected as the classified product. However, the wet classification device is preferably operated at a centrifugal force of 1 to 100 G, preferably 2 to 50 G, for 0.1 to 100 minutes, preferably 0.4 to 30 minutes.

The reason why, in this step, the sediment containing porous silica-based particles having diameters of more than 30 µm is separated and removed is that for obtaining the porous silica-based particles having an average particle diameter of not more than 30 µm. When the average particle diameter of the porous silica-based particles is more than 30 µm, upon applying a powder of such particles onto the skin, most of the panelists as described above will feel to be harsh and grating.

A wet classification method for porous silica-based particles has been described above. In the present invention, it is a matter of course that the order of the operation in the wet classification of the porous silica-based particles can be reversed. Specifically, in the present invention, a method may be adopted in which porous silica-based particles having diameters of more than 30 µm are first separated and removed in the step (d), and porous silica-based particles having diameters of less than 0.5 µm are then separated and removed in the step (c).

Step (e)

In this step, a cake-like substance of porous silica-based particles is prepared by filtering the dispersion obtained in the step (d) to separate solid material.

The dispersion can be filtered through a commercially available device by a conventional method, and examples thereof include Buchner funnels, filter presses, horizontal belt filters, Synchro™ filters, precoat filters, drum filters, belt filters, tray filters, and centrifugal separators.

Further, preferably, the cake-like substance is satisfactorily washed with pure water such as an ion-exchange water or a distilled water, before the subsequent step.

Step (f)

In this step, a dried powder of porous silica-based particles having an average particle diameter of 0.5 to 30 µm is prepared by drying and then crushing or breaking up the cake-like substance obtained in the step (e).

Preferably, the cake-like substance is dried under the atmosphere pressure or the reduced pressure at a temperature of room temperature to 200° C., preferably 50 to 150° C., for 1 to 24 hours, preferably 2 to 12 hours. When the drying temperature is below the room temperature, the cake-like substance will not be satisfactorily dried. On the other hand, from the viewpoint of cost effectiveness, in order to obtain a dried powder of the particles, there is no need to adopt a temperature above 200° C., because a satisfactory drying effect can be attained at a drying temperature of 200° C. or below. When the drying time is less than one hour, in some cases, the cake-like substance will not be satisfactorily dried. On the other hand, from the viewpoint of cost effectiveness, in order to obtain a dried powder of the particles, there is no need to adopt a drying time of more than 24 hours, because the cake-like substance can be satisfactorily dried even when the drying time is not more than 24 hours.

The dried powder of the porous silica-based particles obtained in the step (f) has a compressive strength of 0.1 to 50 kgf/mm$^2$.

Accordingly, when the porous silica-based particles are used in applications where high compressive strength is required, the dried powder of the porous silica-based particles should be calcined. Specifically, the dried powder of the porous silica-based particles obtained in the step (f) is preferably calcined at a temperature of 200 to 800° C. for 1 to 24 hours. When the calcining temperature is less than 200° C., the siloxane bonding among primary particles (i.e., fine silica-based particles) constituting the porous silica-based particles is not satisfactory and, thus, an improvement in compressive strength may not be expected. On the other hand, when the calcining temperature is more than 800° C., the pores or caves existing in the particles may be disappeared or decreased due to sintering of the particles, which makes it difficult to maintain a desired porosity, and sometimes results in the production of crystalline silica (such as quartz). On the other hand, when the calcining time is less than one hour, the siloxane bonding among primary particles (i.e., fine silica-based particles) constituting the porous silica-based particles is not satisfactory and, thus, an improvement in compressive strength may not be expected. On the other hand, even when the calcining time exceeds 24 hours, no particular effect can be attained and, thus, the cost effectiveness is not good.

When the dried powder of the porous silica-based particles is calcined under the above conditions, porous silica-based particles having a compressive strength of 0.5 to 100 kgf/mm$^2$ are obtained.

Thus, depending upon the contemplated application, the dried powder or calcined powder of the porous silica-based particles may be properly selected and used.

In the prior art, there are many cases that the dried powder of the porous silica-based particles obtained in the step (a) or the calcined powder prepared by calcining the dried powder is supplied for treatment to a dry classification device with a cyclonic separation. The use of this dry classification method, however, is disadvantageous in that, although a dried or calcined powder of porous silica-based particles which have a regulated particle size distribution and have a desired CV value may be obtained, in some cases, for example, small particles and the like attached to the surface of the particles will not be completely removed and, further, during the operation of the dry classification, the surface smoothness of the particles can be significantly lowered due to disintegration of the particles by collision among the particles or by collision against the side wall of the apparatus in the dry classification device (this tendency is particularly significant when the powder is a dried powder) and abrasion of the surface of the particles by friction.

The present inventors have subjected the dry classified product to the treatment in the step (b) according to the present invention, and further to the treatment in the steps (c) and (d) and, as a result, have found that, as can be seen from photographs taken by a scanning electron microscope (SEM) with a magnifying power of 3,000 (FIG. 5) and with a magnifying power of 10,000 (FIG. 6), concaves and convexes produced (for example, by attached foreign matters and by a surface abrasion) on the surface of the particles will not be repaired. Accordingly, it has been found that the dry classification device should not be used for the production of porous silica-based particles having a smooth surface.

Further, it has been found that, for not only the particles treated in the dry classification device, but also a calcined product obtained by heat treatment at a temperature of 200° C. or above, it is difficult to remove foreign matters such as small particles attached to the surface of the particles.

In the specification of the present invention, the method for treating the porous silica-based particles obtained by spray-drying with use of a spray dryer has been described above. It is a matter of course that the porous silica-based particles obtained by the emulsion method may be treated in the steps (b) to (f) according to the present invention (if necessary further including the calcination step). That is, porous silica-based particles, obtained by this method, that have an average particle diameter of 0.5 to 30 µm and have a smooth surface also fall within the scope of the present invention.

The porous silica-based particles obtained above may, if necessary, be ultrasonically treated as long as damage such as abrasion or disintegration to the particles does not occur. However, it is considered that there is substantially no necessity of conducting the ultrasonic treatment.

[Cosmetic]

The cosmetics according to the present invention will be described below in more detail. However, it should be noted that the present invention is not necessarily limited to these cosmetics.

The cosmetics according to the present invention are produced by blending the porous silica-based particles with various cosmetic ingredients which will be described later.

The amount of the porous silica-based particles blended into the cosmetic according to the present invention may vary depending, for example, upon the type of the cosmetic to be prepared and cosmetic ingredients to be blended, but is 0.1 to 30% by weight, preferably 1 to 10% by weight, based on the cosmetic. When the blending amount of the porous silica-based particles is less than 0.1% by weight, as the feeling-improving effect will not be obtainable, it becomes unpractical. On the other hand, when the blending amount is more than 30% by weight, long lasting performance of the cosmetic is not expected.

Examples of various cosmetic ingredients include fats and oils such as olive oils, rape-seed oils, and beef tallows; waxes such as jojoba oils, carnauba waxes, candelilla waxes, and beeswaxes; hydrocarbons such as paraffins, squalanes, synthetic and botanical squalanes, α-olefin oligomers, microcrystalline waxes, pentane, and hexane; fatty acids such as stearic acid, myristic acid, oleic acid, and α-hydroxy acid; alcohols such as isostearyl alcohol, octyldodecanol, lauryl alcohol, ethanol, isopropanol, butyl alcohol, myristyl alcohol, cetanol, stearyl alcohol, and behenyl alcohol; alkyl glyceryl ethers; esters such as isopropyl myristate, isopropyl palmitate, ethyl stearate, ethyl oleate, cetyl laurylate, and decyl oleate; polyhydric alcohols such as ethylene glycol, triethylene glycol, polyethylene glycol, propylene glycol, glycerin, and diglycerin; succharides such as sorbitol, glucose, sucrose, and trehalose; silicone oils such as methyl polysiloxane, methyl hydrogen polysiloxane, methylphenyl silicone oils, various modified silicone oils, and cyclic dimethyl silicone oils; silicone gels crosslinked by silicone and/or other organic compound; nonionic, cationic, anionic, or amphoteric various surfactants; fluorine oils such as perfluoropolyethers; various polymers such as gum arabic, carageenan, agar, xanthan gum, gelatin, alginic acid, guar gum, alubumin, pullulan, carboxy vinyl polymer, cellulose and derivatives thereof, polyacrylamide, sodium polyacrylate, and polyvinyl alcohol; various surfactants of anionic, cationic, or nonionic type; extracts of animals and plants; amino acids and peptides; vitamins; ultraviolet light protecting agents such as cynnamic acid-type agents, salicylic acid-type agents, benzoic acid ester-type agents, urocanic acid-type agents, benzophenone-type agents, and octyl paramethoxy cynnamate; antiseptic/preservative agents; antioxidants; modified or unmodified clay minerals; solvents such as butyl acetate, acetone, and toluene; titanium oxide, zinc oxide, aluminum oxide, aluminum hydroxide, iron oxide red, yellow iron oxide, black iron oxide, cerium oxide, zirconium oxide, silica, mica, talc, sericite, boron nitride, barium sulfate, and titanated mica having pearl-like gloss, and their composites, which have various particle diameters, particle size distributions, and shapes; various organic pigments and dyes; water; and perfumes.

Inorganic compounds such as titanium oxide or zinc oxide as described above may be those having a surface previously subjected to silicon treatment, fluorine treatment, metallic soap treatment or the like.

The cosmetic may contain resin particles such as polymethylmethacrylate, nylon, silicone resin, silicone rubber, polyethylene, polyester, or polyurethane particles.

Further, arbutin, kojic acid, vitamin C, sodium ascorbate, magnesium ascorbyl phosphate, ascorbyl dipalmitate, ascorbyl glucoside, other ascorbic acid derivatives, placental extracts, sulfur, botanical extracts such as oil-soluble licorice extracts and mulberry bark extracts, linoleic acid, linolenic acid, lactic acid, or tranexamic acid may be incorporated as active ingredients having a whitening effect.

Furthermore, active ingredients having an antiaging effect such as vitamin C, cartenoid, flavonoid, tannin, camphor derivatives, lignan, saponin, retinoic acid and retinoic acid structural analogs, N-acetylglucosamine, and α-hydroxy acid; polyhydric alcohols such as glycerin, propylene glycol, and 1,3-butylene glycol; saccharides such as mixed isomerized sugar, trehalose, and pullulan; biopolymers such as sodium hyaluronate, collagen, elastin, chitin/chitosan, and sodium chondroitin sulfate; amino acids, betaine, ceramide, sphingolipid, cholesterol, and derivatives thereof; ε-aminocapronic acid; glycyrrhetinic acid; or various vitamins may be incorporated as active ingredients having a roughened skin amelioration effect.

Further, in the present invention, cosmetic ingredients described, for example, in Japanese Standards of Quasi-drug Ingredients 2006 (issued by YAKUJI NIPPO LIMITED, on Jun. 16, 2006) and International Cosmetic Ingredient Dictionary and Handbook (issued by The Cosmetic, Toiletry, and Fragrance Association, Eleventh Edition 2006) can be used without particular limitation.

The cosmetics according to the present invention can be produced by conventional methods.

The cosmetics produced by the conventional methods may be used in various forms such as powder, cake, pencil, stick, cream, gel, mousse, liquid, and cream forms, and specific examples thereof include cleaning cosmetics such as soaps, cleansing foams, and makeup removing creams; skin care cosmetics, for example, for moisture retention/rough skin prevention, acne, care for keratin, massage, wrinkles/flabbiness, drabness/shadow, ultraviolet care, whitening, and antioxidation care; base makeup cosmetics such as powder foundations, liquid foundations, cream foundations, mousse foundations, pressed powders, and makeup bases; point makeup cosmetics such as eye shadows, eye blows, eyeliners, mascaras, and lip glosses; haircare cosmetics, for example, for hair restoration, scurf prevention, itchiness prevention, cleaning, conditioning/styling, permanent/waving, and hair coloring/hair bleaching; body care cosmetics such as for cleaning, sunscreen, skin care, slimming, blood circulation improvement, itchiness inhibition, body odor prevention, hidroschesis, skin hair care, and repellent and body powder; fragrance cosmetics such as perfumeries, eau de perfumes, eau de toilettes, eau de colognes, shower colognes and the like, solid perfumes, body lotions, and bath oils; and oral care products such as toothbrushings and mouthwashes.

[Measuring Methods]

Measuring methods adopted in working examples and the like in the present invention will be specifically described.

(1) Average Particle Diameter of Porous Silica-Based Particles

A slurry liquid with a solid content of 0.1 to 5% by weight is prepared by mixing a powder of porous silica-based particles with an aqueous solution containing glycerin of 40% by weight. Then, the slurry liquid is subjected to an ultrasonic generation apparatus (model US-2, manufactured by iuch) where the slurry liquid is treated for five minutes to obtain a dispersed liquid thereof. Next, a sample is extracted from the dispersed liquid to which the aqueous solution containing glycerin may be added for adjustment of the solid content thereof. The sample is placed in a glass cell (a size of length 10 mm, width 10 mm, and height 45 cm), and by using such a cell, the average particle diameter of the porous silica-based particles is measured with use of a centrifugal sedimentation type particle size distribution analyzer (CAPA-700, manufactured by HORIBA, Ltd.).

(2) Average Particle Diameter of Fine Silica-Based Particles

The specific surface area S ($m^2/g$) of the fine silica-based particles is measured by an NaOH titration method, and the average particle diameter is calculated by the following equations:

From $S=[4\pi(D/2)^2 \times (10^{-9})^2]/[(4\pi \times (D/2)^3/3 \times G \times (10^{-7})^3)]$, $D=6,000/(S \times 2.2)$, wherein "D" represents an average particle diameter of the fine silica-based particles (nm); "S" represents a specific surface area thereof ($m^2/g$); and "G" represents the specific gravity of amorphous silica, the value of which is 2.2 $g/cm^3$.

(3) Surface Smoothness of Porous Silica-Based Particles

A powder of porous silica-based particles is subjected to vapor deposition of gold in a vacuum vapor deposition device (JFC-1200, manufactured by JEOL LTD.) at a degree of vacuum of 8 Pa for 40 seconds to prepare a sample. A photograph of the sample is then taken by a scanning electron microscope (SEM) (JSM-5600, manufactured by JEOL LTD.) with a magnifying power of 10,000 at an accelerated voltage of 15 kV. Further, samples of more than 100 particles randomly picked out are, using the SEM photograph, visually observed for the presence or absence of foreign matters such as small particles with a nanosize attached to the surface of the porous silica-based particles, and the number of particles for which six (6) or more of the small particles are seen per $\mu m^2$ of the plane surface on the porous silica-based particles is visually counted. Then, a surface smoothness (%) is calculated by the following equation:

Surface smoothness (%)=$(T-P)/T \times 100$, wherein "T" represents the total number of the particles observed; and "P" represents the counted number of the particles for which the foreign matters as described above have been seen.

(4) Surface Roughness Value of Porous Silica-Based Particles 0.1 g of a powder of porous silica-based particles is homogeneously mixed with about 1 g of an epoxy resin (EPO-KWICK, manufactured by BUEHLHER), and the mixture is cured at room temperature. Thereafter, the cured product is subjected to a section processing of a 20 μm area by a gallium-ion sputtering with an FIB machine (FB-2100, manufactured by Hitachi, Ltd.) to prepare a sample with a section having a thickness of 100 to 200 nm. Next, a photograph of a cross-section of the sample is taken by a transmission electron microscope (TEM) (HF-2200, manufactured by Hitachi, Ltd.) with a magnifying power of 100,000 at an accelerated voltage of 200 kV. Further, for each of any ten microphotographs, a difference between the circumscribed circle and the inscribed circle at a boundary of the particle is measured, and the average of the measured data is regarded as the surface roughness value.

(5) Non-Sphericity of Porous Silica-Based Particles

As with the above (3), photographs are taken by a scanning electron microscope (SEM) (JSM-5600, manufactured by JEOL LTD.) with magnifying powers of 1,000 to 3,000. Further, for each of any 100 or more particles, a longer diameter with the almost longest dimension (DL) and a shorter diameter with the almost shortest dimension (DS) thereof are measured from the SEM photograph for each particle, and then a different rate showing a difference between the dimensions DL and DS is calculated by the following equation; (That is, if the dimension DL is equal to the dimension DS, the different rate becomes 0% and the particle thereof is regarded as that with a 100% sphericity.)

Different rate (%)=$(DL-DS)/DL \times 100$

Then, the number ($N_x$) of non-spherical particles (including particles having a distorted shape) with a different rate as described above being not less than 5%, and the number ($N_y$) of agglomerated particles formed by agglomeration among the particles are counted, and the non-sphericity is calculated based on the counted data in accordance with the following equation;

Non-sphericity (%)=$(N_x+N_y)/N \times 100$, wherein "N" represents the total number of the particles observed; "$N_x$" represents the counted number of the non-spherical particles as described above, and "$N_y$" represents the counted number of the agglomerated particles as described above.

(6) Coefficient of Variation in Porous Silica-Based Particles (CV Value)

As with the above (3), photographs are taken by a scanning electron microscope (SEM) (JSM-5600, manufactured by JEOL LTD.) with magnifying powers of 1,000 to 3,000. Further, for images of any 2,000 or more particles, the average particle diameter is measured with an image analyzing system (IP-1000, manufactured by Asahi Kasei Corporation), and the coefficient of variation (CV value) regarding the particle size distribution is calculated. Specifically, for each of 2,000 particles, the particle diameter is measured, and the average particle diameter ($D_n$) and standard deviation (a) of the particle diameters are determined based on the measured particle diameters, and then the coefficient of variation (CV value) is calculated by the following equation:

Coefficient of variation (CV value)=$\sigma/D_n \times 100$, wherein "$\sigma$" represents a standard deviation of the porous silica-based particles; and "$D_n$" represents an average particle diameter thereof.

(7) Specific Surface Area of Porous Silica-Based Particles

About 30 ml of a powder of porous silica-based particles is put in a magnetic crucible (model B-2), and is dried at a temperature of 105° C. for 2 hours. Then, the dried powder is placed in a desiccators, and is cooled to room temperature. Next, 1 g of a sample is weighed, and the specific surface area ($m^2/g$) of the sample is measured by a BET method with a full-automatic surface area measuring apparatus (Multisorb 12, manufactured by YUASA-IONICS COMPANY, LIMITED).

(8) Pore Volume of Porous Silica-Based Particles

About 10 g of a powder of porous silica-based particles is put in a crucible, and is dried at a temperature of 105° C. for one hour. Then, the dried powder is placed in a desiccators, and is cooled to room temperature. Next, 1 g of a sample is weighed in a well cleaned cell, nitrogen is adsorbed on the sample with use of a nitrogen adsorption device (manufactured by JGC Catalysts and Chemicals Ltd.), and the pore volume is calculated by the following equation:

$$\text{Pore volume (ml/g)} = R \times (V - Vc)/W,$$

wherein "V" represents an adsorption amount (ml) in a standard state at a pressure of 735 mmHg; "Vc" represents the volume of a cell blank (ml) at a pressure of 735 mmHg; and "W" represents the weight of the sample (g); and "R" represents the density ratio of nitrogen gas to liquid nitrogen, the value of which is 0.001567.

(9) Oil Absorption Rate of Porous Silica-Based Particles 1.5 g of a powder of porous silica-based particles is placed on a glass measuring plate. Next, a boiled linseed oil (as specified in JIS K 5101) is dropped by 4 or 5 droplets for each dropping onto the sample through a burette, and the whole mixture is kneaded with a spatula. The dropping of the oil and the kneading are repeated, and the formation of a helically wound state is regarded as an end point. The oil absorption rate is calculated by the following equation.

$$\text{Oil absorption rate (ml/100 g)} = (A/W) \times 100,$$

wherein "A" represents the dropped amount of the boiled linseed oil (ml); and "W" represents the weight of the sample (g).

(10) Compressive Strength of Porous Silica-Based Particles

One particle which falls within a range of an average particle diameter ±0.5 μm is picked out as a sample from a powder of the porous silica-based particles. Then, a load is applied at a given loading rate to the sample with use of a micro compression tester (MCTM-200, manufactured by SHIMADZU CORPORATION), and the weighted value when the particle is collapsed is regarded as the compressive strength (kgf/mm$^2$) for the particle. Further, this operation is repeated four times to measure the compressive strength for five samples. The measured values are averaged, and the average thus obtained is regarded as the compressive strength of the particle.

(11) pH of Dispersion Containing Porous Silica-Based Particles

A dispersion prepared by dispersing porous silica-based particles obtained by spray-drying in water or a dispersion after adjustment of pH by the addition of ammonia or the like to the dispersion is stirred in a thermostatic chamber of 25° C. for at least 30 minutes, and a glass electrode of a pH meter (F22, manufactured by HORIBA, Ltd.) corrected with standard solutions each having pH of 4, 7 and 9 is then inserted into the dispersion to measure pH thereof.

(12) Drying Loss and Ignition Loss of Porous Silica-Based Particles 1 g of a powder of porous silica-based particles is dried at a temperature of 105° C. for 2 hours. The drying loss (%) is calculated from the weight reduced by the drying and the weight (1 g) before the drying. Whilst, 1 g of a powder of the porous silica-based particles is calcined at a temperature of 850° C. for 30 minutes. The ignition loss (%) is calculated from the weight reduced by the calcining and the weight (1 g) before the calcining.

According to the present invention, it is preferable that the drying loss is not less than 2% by weight and the ignition loss is not less than 5% by weight. Specifically, the present inventors have found that, when the drying loss is less than 2% by weight or when the ignition loss is less than 5% by weight, it is difficult to remove the small particles and the like attached to the surface of the porous silica-based particles. Accordingly, in the present invention, these numerical values are used as an index.

(13) Silica Purity of Porous Silica-Based Particles

About 10 g of a powder of porous silica-based particles is heated at 850° C. for 30 minutes, and after cooled it down to room temperature, 0.8 g of the heated powder is accurately weighed. Then, 20 ml of hydrochloric acid is mixed with the weighed powder, and the mixture is heated to dryness on a sand bath. Further, the residue is moistened with hydrochloric acid, and the moistened residue is heated to dryness on the sand bath, and is then heated at 110 to 120° C. for 2 hours. Subsequently, the sample is cooled down to room temperature, 5 ml of diluted hydrochloric acid is added, and the mixture is heated. Then, the heated mixture is cooled down to room temperature, 20 to 25 ml of hot water is added, and the solution is immediately filtered. The residue is washed with warm water until the wash liquid no longer exhibits a reaction of the chloride. The residue together with a filter paper is then placed in a platinum crucible and is ignited until ashing, is further ignited for 30 minutes and is cooled down to room temperature. The weight of the ash is measured, and the purity of silica ($SiO_2$ content) is calculated.

(14) Zeta Potential of Porous Silica-Based Particles

A dispersion prepared by dispersing porous silica-based particles obtained by spray-drying in water or a dispersion after adjustment of pH by the addition of ammonia or the like to the dispersion is subjected to a zeta potential measurement apparatus based on an ultrasonic attenuation spectroscopy method (DT-1200, manufactured by Dispersion Technology Inc.) where the zeta potential of the particles contained in the dispersion is measured.

(15) Feeling Test of Porous Silica-Based Particles

A powder of porous silica-based particles is subjected to a sensory test by 20 expert panelists, and hearing investigations are performed for seven evaluation items, namely, about the feeling properties of smoothness, moistness, rolling effect, even spreadability, adhesiveness to the skin, sustainability of the rolling effect and a degree of grating which is inherent in silica-based particles. The results are evaluated on each item in accordance with the following criteria (a) for scoring. Next, the total of the scores recorded by the panelists is calculated, and the feeling of the porous silica-based particles is evaluated on each item in accordance with the following criteria (b) for evaluation.

Criteria (a) for Scoring
5: Excellent
4: Good
3: Fair
2: Poor
1: Failed

Criteria (b) for Evaluation
⊚: A total score of not less than 80
○: A total score of not less than 60 and less than 80
Δ: A total score of not less than 40 and less than 60
▲: A total score of not less than 20 and less than 40
x: A total score of less than 20

(16) Feeling Test of Powder Foundation

A powder foundation blended with a powder of porous silica-based particles is subjected to a sensory test by 20 expert panelists, and hearing investigations are performed for six evaluation items, namely, about the feeling properties of (1) even spreadability, moistness, and smoothness during applying it onto the skin, and (2) uniformity, moistness, and softness of a cosmetic film after the applying onto the skin. The results are evaluated on each item in accordance with the following criteria (a) for scoring. Next, the total of the scores recorded by the panelists is calculated, and the feeling of use of the foundation is evaluated on each item in accordance with the following criteria (b) for evaluation.

Criteria (a) for Scoring
5: Excellent
4: Good
3: Fair
2: Poor
1: Failed
Criteria (b) for Evaluation
⊚: A total score of not less than 80
○: A total score of not less than 60 and less than 80
△: A total score of not less than 40 and less than 60
▲: A total score of not less than 20 and less than 40
×: A total score of less than 20

EXAMPLES

The following Examples further illustrate the present invention. The present invention, however, is not to be construed as being limited thereto.

Example 1

Step (a)

A silica sol containing fine silica-based particles having an average particle diameter of 15 nm (Cataloid S-20L, $SiO_2$ content 20% by weight, manufactured by JGC Catalysts and Chemicals Ltd.) was subjected to a spray dryer (NIRO ATMIZER, manufactured by NIRO LTD.) for spray-drying under conditions of an inlet temperature of 240° C., an outlet temperature of 55° C., and a spraying speed of 2 liters/minutes to give Dried Powder 1A of porous silica-based particles having an average particle diameter of 5 μm.

For Dried Powder 1A of porous silica-based particles thus obtained, the average particle diameter, coefficient of variation of particles, drying loss, and ignition loss were measured by the above measuring methods. The results are shown in Table 1.

Figure 1:
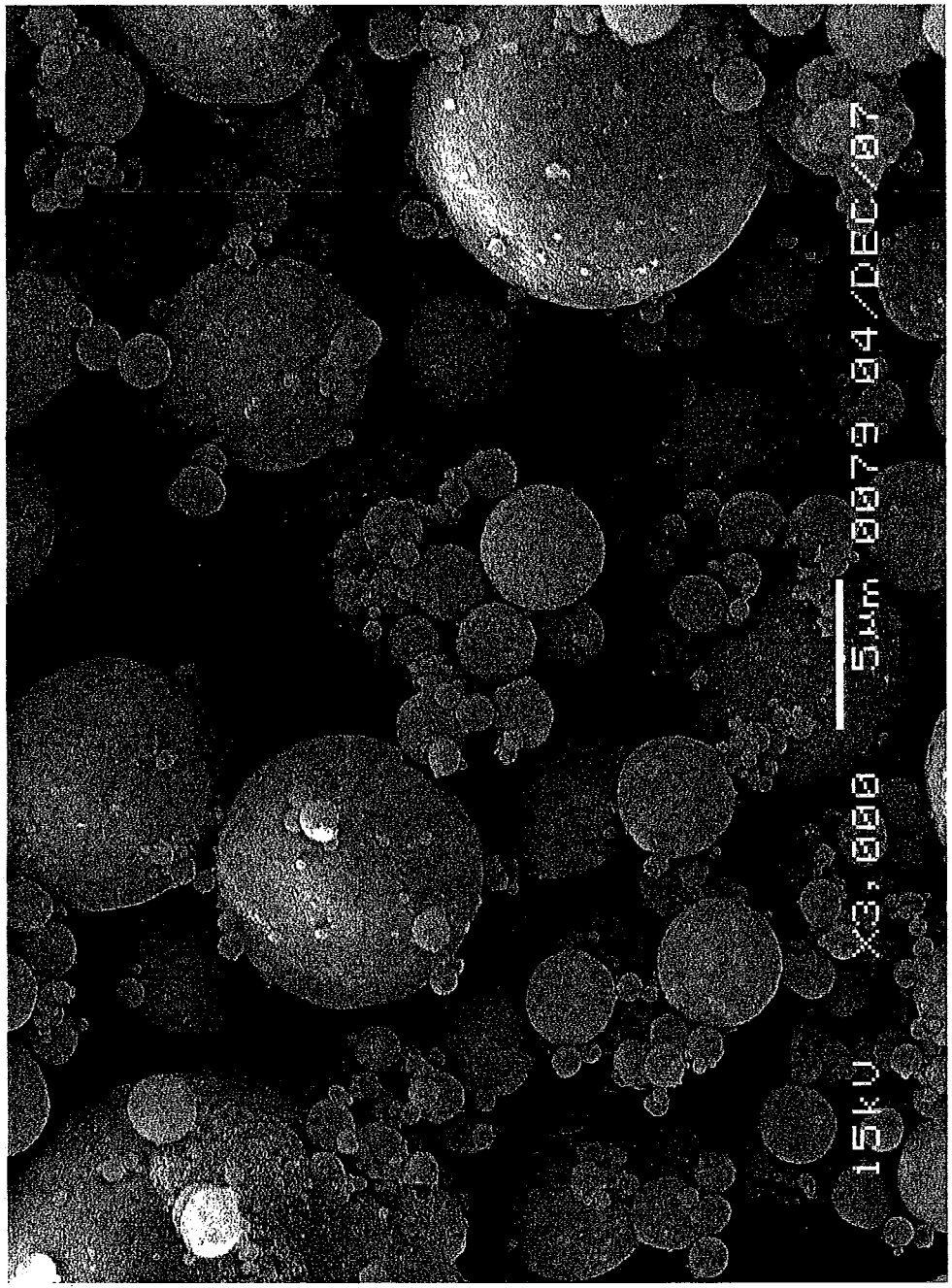
FIG. 1 is a photograph of porous silica-based particles, which were obtained in step (a) (that is, a spray-drying step) in Example 1, taken by a scanning electron microscope (SEM) with a magnifying power of 3,000.

Further, for Dried Powder 1A of porous silica-based particles, the state of the particle surface was observed by a scanning electron microscope with magnifying powers of 3,000 and 10,000. As a result, for observation with both the magnifying powers, foreign matters such as small particles were seen on the particle surface. Photographs taken by an electron microscope (SEM) at that time are shown in FIG. 1 (magnifying power: 3,000) and FIG. 2 (magnifying power: 10,000).

Step (b)

2,160 cc of pure water was added to 240 g of Dried Powder 1A of porous silica-based particles obtained in the step (a) above, and the mixture was adjusted to pH 8 by the addition of aqueous ammonia, followed by stirring at a rotating speed of 300 rpm for 2 hours to give Dispersion (1) having a solid content of 10% by weight. The zeta potential of the particles contained in Dispersion (1) was measured and found to be −35 mV.

Step (c)

Dispersion (1) obtained in the step (b) above was put in four centrifugal cans with a capacity of 700 cc (600 g of the dispersion for each can) and was centrifuged with a centrifugal separator (CF7D2, rotor: RT3S3, manufactured by Hitachi Koki Co., Ltd.) under conditions of a temperature of room temperature, a rotating speed of 500 rpm (corresponding to a centrifugal acceleration of 48.6 G), and a time of 370 seconds (6.2 minutes), so that particles mainly having particle diameters of not less than 2.5 μm are sedimented or settled. Next, a supernatant containing porous silica-based particles mainly having particle diameters of not more than 2.5 μm was gently extracted, separated, and removed. Then, 600 cc of pure water, the pH of which was adjusted to 8 by adding an aqueous ammonia therein, was mixed with the sediment or precipitate (including a residual liquid) for each can, and the mixture was stirred for 2 hours.

Further, the centrifugal operation was again performed at a rotating speed of 500 rpm (corresponding to a centrifugal acceleration of 48.6 G) for 370 seconds (6.2 minutes) for each can. A supernatant containing porous silica-based particles mainly having particle diameters of not more than 2.5 μm was then gently extracted, separated, and removed. Then, 600 cc of pure water was mixed with the sediment or precipitate, and the mixture was stirred for one hour to give Dispersion (2) containing porous silica-based particles mainly having particle diameters of 2.5 to 50 μm.

Step (d)

Dispersion (2) obtained in the step (c) above was centrifuged by a centrifugal separator (CF7D2, rotor: RT3S3, manufactured by Hitachi Koki Co., Ltd.) under conditions of a temperature of room temperature, a rotating speed of 300 rpm (corresponding to a centrifugal acceleration of 17.5 G), and a time of 64 seconds (1.1 minutes) so that particles mainly having particle diameters of more than 10 μm are sedimented or settled for each can. Next, a supernatant containing porous silica-based particles mainly having particle diameters of 2.5 to 10 μm was gently extracted to separate and remove a liquid containing the sediment or precipitate of porous silica-based particles mainly having particle diameters of 10 to 50 μm, and then the supernatant obtained from each of four centrifugal cans was mixed. Thus, Dispersion (3) containing porous silica-based particles having particle diameters of 2.5 to 10 μm was obtained.

Step (e)

Dispersion (3) obtained in the step (d) above was filtered through a quantitative filter paper (No. 5C, manufactured by Advantec Toyo Kaisha, Ltd.) using a Buchner funnel (3.2 L, manufactured by Sekiya Chemical Glass Apparatus Co. Ltd.), followed by repeated washing with pure water to obtain a cake-like substance.

Step (f)

The cake-like substance obtained in the step (e) above was dried at a temperature of 110° C. for 5 hours. The dried powder was then subjected to a juicer mixer (manufactured by Hitachi, Ltd.) for crushing or breaking-up some of the lump to obtain Dried Powder 2A of porous silica-based particles (hereinafter referred to as "Example Dried Powder 2A").

For Example Dried Powder 2A thus obtained, the average particle diameter, coefficient of variation of particles, surface smoothness, surface roughness, non-sphericity, specific surface area, oil absorption rate, pore volume, compressive strength, silica purity, drying loss, and ignition loss were determined by the above measuring methods. The results are shown in Table 3.

Further, for Example Dried Powder 2A, the state of the surface of particles was observed by a scanning electron microscope with magnifying powers of 3,000 and 10,000. As a result, for both the magnifying powers, foreign matters such as small particles attached to the particle surface could be hardly seen. For Example Dried Powder 2A, the carbon content was measured with a carbon/sulfur analyzer (EMIA-320 V: manufactured by HORIBA, Ltd.) and found to be below the detection limit (100 ppm).

Calcination Step

Example Dried Powder 2A obtained in the step (f) above was calcined at a temperature of 450° C. for three hours to obtain Calcined Powder 3A of porous silica-based particles (hereinafter referred to as "Example Calcined Powder 3A").

For Example Calcined Powder 3A thus obtained, the average particle diameter, coefficient of variation of particles, surface smoothness, surface roughness, non-sphericity, specific surface area, oil absorption rate, pore volume, compressive strength, silica purity, drying loss, and ignition loss were determined by the above measuring methods. The results are shown in Table 4.

Figure 3:
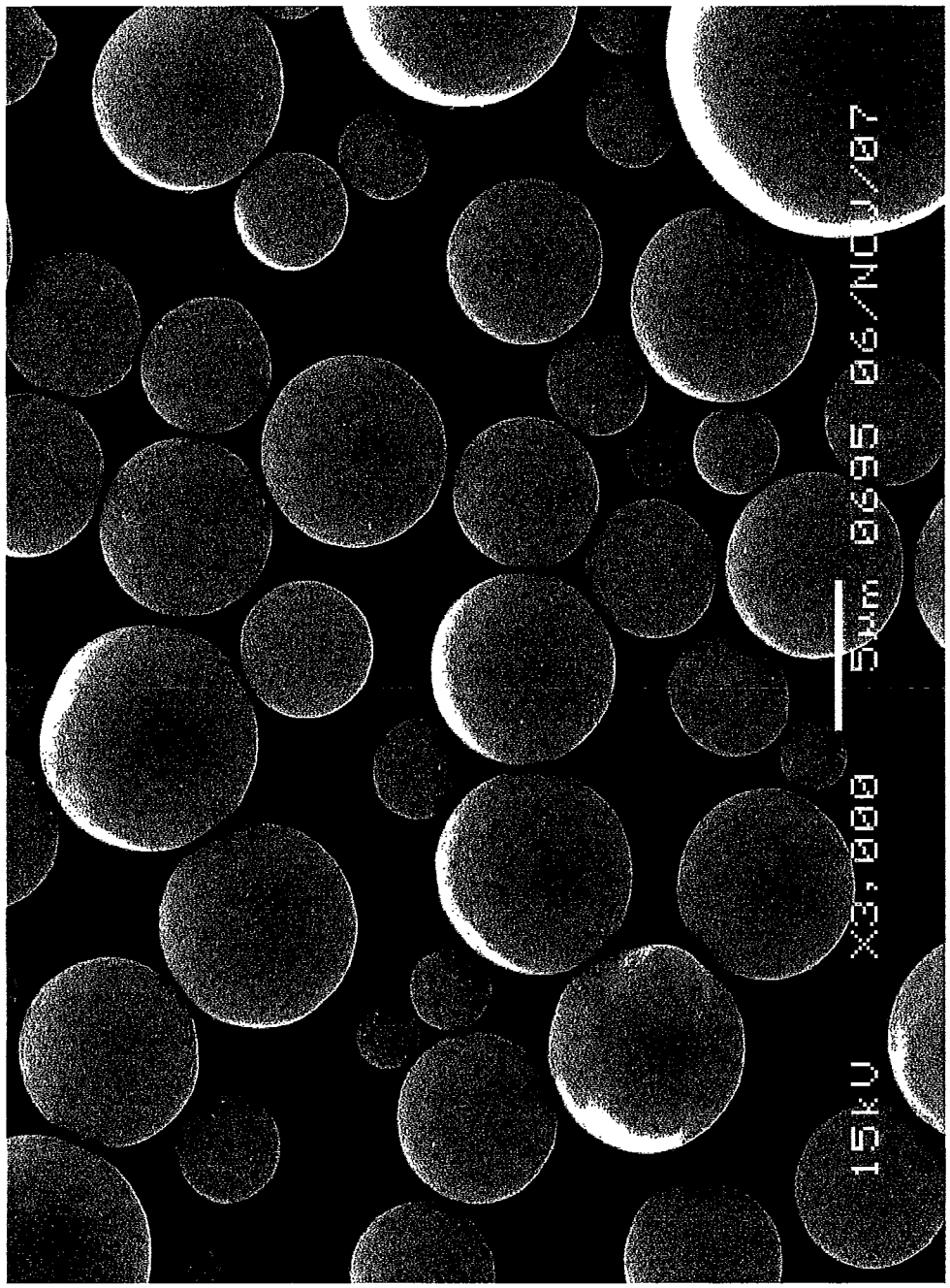
FIG. 3 is a photograph of porous silica-based particles, which were obtained in a calcination step in Example 1 (i.e., the particles produced by calcining a dried powder of porous silica-based particles classified under a wet condition), taken by a scanning electron microscope (SEM) with a magnifying power of 3,000.

Further, for Example Calcined Powder 3A, the state of the surface of particles was observed by a scanning electron microscope with magnifying powers of 3,000 and 10,000. As a result, for both the magnifying powers, foreign matters such as small particles attached to the particle surface could be hardly seen. Photographs taken by an electron microscope (SEM) at that time are shown in FIG. 3 (magnifying power: 3,000) and FIG. 4 (magnifying power: 10,000).

When the cross-section of a particle of the calcined powder of the porous silica-based particles was observed by a transmission electron microscope with a magnifying power of 100,000, foreign matters such as small particles could be hardly seen at a boundary of the particle. Further, a surface roughness value defined by a difference between a circumscribed circle and an inscribed circle of the particle was determined from a photograph taken at that time by an electron microscope (TEM) and was found to be not more than 10 nm. The photograph taken by the electron microscope (TEM) is shown in FIG. 11.

Examples 2 to 5

Dried Powders 1B to 1E of porous silica-based particles shown in Table 1 were obtained by spray-drying silica sols in the same manner as in Example 1, except that, instead of the silica sol used in Example 1, dispersions of fine silica-based particles containing fine silica-based particles manufactured by JGC Catalysts and Chemicals Ltd. and manufactured by NIPPON AEROSIL CO., LTD. shown in Table 1 were used and some of spray-drying conditions were varied dependent upon the necessity.

The operation of the steps (b) to (f) above in Example 1 was then performed under conditions shown in Table 2 to obtain Dried Powders 2B to 2E of porous silica-based particles (hereinafter referred to as "Example Dried Powders 2B to 2E").

For Example Dried Powders 2B to 2E thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 3.

Further, for Example Dried Powders 2B to 2E, the state of the surface of particles was observed by a scanning electron microscope with magnifying powers of 3,000 and 10,000. As a result, for both the magnifying powers, foreign matters such as small particles attached to the particle surface could be hardly seen.

Next, Example Dried Powders 2B to 2E thus obtained were calcined under the same conditions as in Example 1 to obtain Calcined Powders 3B to 3E of porous silica-based particles (hereinafter referred to as "Example Calcined Powders 3B to 3E").

For Example Calcined Powders 3B to 3E thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 4.

Further, for Example Calcined Powders 3B to 3E, the state of the surface of particles was observed by a scanning electron microscope with magnifying powers of 3,000 and 10,000. As a result, for both the magnifying powers, foreign matters such as small particles attached to the particle surface could be hardly seen.

Examples 6 and 7

The dispersion of fine silica-based particles containing the fine silica-based particles ($SiO_2$ content: 100% by weight) used in Example 5 and an aqueous solution of silicic acid (containing 5% by weight of a silicon compound in terms of $SiO_2$) were mixed together at weight ratios shown in Table 1, followed by additional stirring for one hour. The mixed dispersions thus obtained were subjected to a spray dryer (NIRO ATMIZER, manufactured by NIRO LTD.) at which spray drying was performed under conditions of an inlet temperature of 240° C., an outlet temperature of 55° C., and a spraying speed of 2 liters/minute to obtain Dried Powders 1F and 1G of porous silica-based particles shown in Table 1.

Next, the operation of the steps (b) to (f) in Example 1 was performed under the same conditions as in Example 1 to obtain Dried Powders 2F and 2G of porous silica-based particles (hereinafter referred to as "Example Dried Powders 2F and 2G").

For Example Dried Powders 2F and 2G thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 3.

Further, for Example Dried Powders 2F and 2G, the state of the surface of particles was observed by a scanning electron microscope with magnifying powers of 3,000 and 10,000. As a result, for both the magnifying powers, foreign matters such as small particles attached to the particle surface could be hardly seen.

Next, Example Dried Powders 2F and 2G thus obtained were calcined under the same conditions as in Example 1 to obtain Calcined Powders 3F and 3G of porous silica-based particles (hereinafter referred to as "Example Calcined Powders 3F and 3G").

For Example Calcined Powders 3F and 3G thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 4.

Further, for Example Calcined Powders 3F and 3G, the state of the surface of particles was observed by a scanning electron microscope with magnifying powers of 3,000 and 10,000. As a result, for both the magnifying powers, foreign matters such as small particles attached to the particle surface could be hardly seen.

For easy comparison, the results of measurement obtained in Example 1 and operating conditions are also shown in Tables 1 to 4 below.

TABLE 1

| | | | Example No. | | | | | | |
|---|---|---|---|---|---|---|---|---|---|
| | | | 1 | 2 | 3 | 4 | 5 | 6 | 7 |
| Prepared Example Dried Powder (spray-dried product) | | | 1A | 1B | 1C | 1D | 1E | 1F | 1G |
| Materials used in spraying | Dispersion of fine silica-based particles (I) | Type of fine silica-based particles | A | A | B | A | C | C | C |
| | | Average diameter of fine particles (nm) | 15 | 15 | 15 | 15 | 7 | 7 | 7 |
| | | Concentration of silica (wt %) | 20 | 20 | 30 | 20 | 100 | 100 | 100 |
| | Aqueous solution of silicic acid (II) | Concentration of silica (wt %) (in terms of $SiO_2$) | — | — | — | — | — | 5 | 5 |
| Sprayed slurry | | Weight mixing ratio of materials used in spraying (I/II) | 100/0 | 100/0 | 100/0 | 100/0 | 100/0 | 40/60 | 10/90 |
| | | Concentration of silica (wt %) | 20 | 20 | 30 | 5 | 7 | 8.1 | 5.5 |
| Spray-drying conditions | | Spraying speed (liter/minutes) | 2 | 4 | 6 | 1 | 2 | 2 | 2 |
| Properties of Example Dried Powder prepared (spay-dried product) | | Average diameter of particles (μm) | 5 | 10 | 20 | 2 | 5 | 5 | 5 |
| | | Coefficient of variation of particles (%) | 87 | 92 | 102 | 75 | 125 | 110 | 67 |
| | | Drying loss of particles (wt %) | 4 | 4 | 4 | 4 | 7 | 4 | 3 |
| | | Ignition loss of particles (wt %) | 7 | 7 | 7 | 7 | 10 | 7 | 6 |

(Note)
Fine silica-based particles A: CATALOID ™ S-20L, manufactured by JGC Catalysts and Chemicals Ltd.
Fine silica-based particles B: CATALOID ™ S-30L, manufactured by JGC Catalysts and Chemicals Ltd.
Fine silica-based particles C: AEROSIL ™ 380, manufactured by NIPPON AEROSIL CO., LTD.
Aqueous solution of silicic acid: manufactured by JGC Catalysts and Chemicals Ltd.

TABLE 2

| | | | | Example No. | | | | | | |
|---|---|---|---|---|---|---|---|---|---|---|
| | | | | 1 | 2 | 3 | 4 | 5 | 6 | 7 |
| | Used Example Dried Powder | | | 1A | 1B | 1C | 1D | 1E | 1F | 1G |
| Operating conditions | Step (b) | pH of dispersion | Before adjustment | 7 | 7 | 7 | 7 | 5 | 5 | 3 |
| | | | After adjustment | 8 | 8 | 8 | 8 | 9 | 9 | 7 |
| | | Zeta potential (mV) | | −35 | −35 | −35 | −35 | −40 | −38 | −46 |
| | | Stirring speed (rpm) | | 300 | 300 | 300 | 300 | 300 | 300 | 300 |
| | | Stirring time (minutes) | | 120 | 120 | 120 | 120 | 480 | 240 | 60 |
| | Step (c) | Centrifugal acceleration (G) | | 49 | 49 | 18 | 1751 | 49 | 49 | 49 |
| | | Operating time (seconds) | | 370 | 90 | 62 | 249 | 370 | 370 | 370 |
| | | Number of times of operation | | 2 | 2 | 2 | 2 | 2 | 2 | 2 |
| | | Diameter of classified particles (μm) | | 2.5 | 5.0 | 10 | 0.5 | 2.5 | 2.5 | 2.5 |
| | Step (d) | Centrifugal acceleration (G) | | 18 | 18 | 1 | 49 | 18 | 18 | 18 |
| | | Operating time (seconds) | | 64 | 16 | 121 | 140 | 64 | 64 | 64 |
| | | Number of times of operation | | 1 | 1 | 1 | 1 | 1 | 1 | 1 |
| | | Diameter of classified particles (μm) | | 10 | 20 | 30 | 4 | 10 | 10 | 10 |

TABLE 3

| | Example No. | | | | | | |
|---|---|---|---|---|---|---|---|
| | 1 | 2 | 3 | 4 | 5 | 6 | 7 |
| Prepared Example Dried Powder | 2A | 2B | 2C | 2D | 2E | 2F | 2G |
| Average particle diameter (μm) | 5 | 10 | 20 | 2 | 5 | 5 | 5 |
| Coefficient of variation of particles (%) | 29 | 26 | 35 | 12 | 30 | 26 | 22 |
| Surface smoothness (%) | 90 | 91 | 89 | 96 | 80 | 85 | 99 |

TABLE 3-continued

|  | Example No. | | | | | | |
| --- | --- | --- | --- | --- | --- | --- | --- |
|  | 1 | 2 | 3 | 4 | 5 | 6 | 7 |
| Surface roughness (nm) | <10 | <10 | <10 | <10 | 15 | <10 | <10 |
| Non-sphericity (%) | 0.5 | 1.2 | 1.8 | 0.1 | 1.9 | 1.2 | 1.0 |
| Specific surface area (m$^2$/g) | 143 | 143 | 143 | 143 | 290 | 188 | 97 |
| Oil absorption rate (ml/100 g) | 57 | 57 | 57 | 57 | 209 | 113 | 24 |
| Pore volume (ml/g) | 0.3 | 0.3 | 0.3 | 0.3 | 1.8 | 0.7 | 0.1 |
| Compressive strength (Kgf/mm$^2$) | 8 | 8 | 6 | 6 | 0.1 | 1 | 49 |
| Silica purity (wt %) | 99.3 | 99.4 | 99.3 | 99.3 | 99.8 | 99.5 | 99.2 |
| Drying loss (wt %) | 0.1 | 0.1 | 0.1 | 0.1 | 0.1 | 0.1 | 0.1 |
| Ignition loss (wt %) | 2.8 | 2.8 | 2.7 | 2.7 | 4.2 | 3.0 | 2.0 |

TABLE 4

|  | Example No. | | | | | | |
| --- | --- | --- | --- | --- | --- | --- | --- |
|  | 1 | 2 | 3 | 4 | 5 | 6 | 7 |
| Prepared Example Calcined Powder | 3A | 3B | 3C | 3D | 3E | 3F | 3G |
| Average particle diameter (μm) | 5 | 10 | 20 | 2 | 5 | 5 | 5 |
| Coefficient of variation of particles (%) | 29 | 26 | 35 | 12 | 30 | 26 | 22 |
| Surface smoothness (%) | 90 | 91 | 89 | 96 | 80 | 85 | 99 |
| Surface roughness (nm) | <10 | <10 | <10 | <10 | 15 | <10 | <10 |
| Non-sphericity (%) | 0.5 | 1.2 | 1.8 | 0.1 | 1.9 | 1.2 | 1.0 |
| Specific surface area (m$^2$/g) | 150 | 150 | 150 | 150 | 320 | 200 | 100 |
| Oil absorption rate (ml/100 g) | 60 | 60 | 60 | 60 | 230 | 120 | 25 |
| Pore volume (ml/g) | 0.3 | 0.3 | 0.3 | 0.3 | 1.8 | 0.7 | 0.1 |
| Compressive strength (Kgf/mm$^2$) | 10 | 10 | 8 | 7 | 1 | 4 | 50 |
| Silica purity (wt %) | 99.3 | 99.4 | 99.3 | 99.3 | 99.8 | 99.5 | 99.2 |
| Drying loss (wt %) | 0.1 | 0.1 | 0.1 | 0.1 | 0.1 | 0.1 | 0.1 |
| Ignition loss (wt %) | 1.4 | 1.2 | 1.3 | 1.2 | 1.8 | 1.6 | 0.4 |

Examples 8 to 10 and Comparative Examples 1 to 5

2,160 cc of pure water was added to 240 g of Dried Powder 1G of porous silica-based particles obtained in the step (a) in Example 7, and dispersions having properties shown in Table 5 were prepared. Further, stirring was performed under conditions shown in Table 5 to prepare Dispersions (1) having a solid content of 10% by weight.

The pH adjustment of the dispersions was performed by the addition of aqueous ammonia having a properly adjusted NH$_3$ concentration.

Next, the operation of the steps (c) to (f) described in Example 1 was performed under the same conditions as in Example 1 to obtain Dried Powders 2H to 2J of porous silica-based particles (hereinafter referred to as "Example Dried Powders 2H to 2J") and Dried Powders 2a to 2e of porous silica-based particles (hereinafter referred to as "Comparative Dried Powders 2a to 2e").

For Example Dried Powders 2H to 2J and Comparative Dried Powders 2a to 2e thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 6.

Further, for Example Dried Powders 2H to 2J, the state of the surface of particles was observed by a scanning electron microscope with magnifying powers of 3,000 and 10,000. As a result, for both the magnifying powers, foreign matters such as small particles attached to the particle surface could be hardly seen.

On the other hand, for Comparative Dried Powders 2a to 2e, the state of the surface of particles was observed by a scanning electron microscope with magnifying powers of 3,000 and 10,000. As a result, for both the magnifying powers, foreign matters such as small particles attached to the particle surface were seen.

Next, Example Dried Powders 2H to 2J and Comparative Dried Powders 2a to 2e thus obtained were calcined under the same conditions as in Example 1 to obtain Calcined Powders 3H to 3J of porous silica-based particles (hereinafter referred to as "Example Calcined Powders 3H to 3J") and Calcined Powders 3a to 3e of porous silica-based particles (hereinafter referred to as "Comparative Calcined Powders 3a to 3e").

For Example Calcined Powders 3H to 3J and Comparative Calcined Powders 3a to 3e thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 7.

Further, for Example Calcined Powders 3H to 3J, the state of the surface of particles was observed by a scanning electron microscope with magnifying powers of 3,000 and 10,000. As a result, for both the magnifying powers, foreign matters such as small particles attached to the particle surface could be hardly seen.

On the other hand, for Comparative Calcined Powders 3a to 3e, the state of the surface of particles was observed by a scanning electron microscope with magnifying powers of 3,000 and 10,000. As a result, for both the magnifying powers, foreign matters such as small particles attached to the particle surface were seen.

TABLE 5

|  |  |  | Example No. | | | Comparative Example No. | | | | |
| --- | --- | --- | --- | --- | --- | --- | --- | --- | --- | --- |
|  |  |  | 8 | 9 | 10 | 1 | 2 | 3 | 4 | 5 |
| Dried Powder to be prepared |  |  | 2H | 2I | 2J | 2a | 2b | 2c | 2d | 2e |
| Operating conditions | pH of dispersion | Before adjustment | 3 | 3 | 3 | 3 | 3 | 3 | 3 | 3 |
|  |  | After adjustment | 5 | 6 | 10 | 7 | 7 | 3 | 13 | 7 |
|  | Zeta potential (mV) | | −24 | −34 | −41 | −46 | −46 | −12 | −8 | −46 |
|  | Stirring speed (rpm) | | 300 | 300 | 300 | 8 | 5000 | 300 | 300 | 300 |
|  | Stirring time (minutes) | | 60 | 60 | 60 | 60 | 60 | 60 | 60 | 1 |

TABLE 6

|  | Example No. | | | Comparative Example No. | | | | |
| --- | --- | --- | --- | --- | --- | --- | --- | --- |
|  | 8 | 9 | 10 | 1 | 2 | 3 | 4 | 5 |
| Prepared Dried Powder | 2H | 2I | 2J | 2a | 2b | 2c | 2d | 2e |
| Average particle diameter (μm) | 5 | 5 | 5 | 5 | 5 | 5 | 5 | 5 |
| Coefficient of variation of particles (%) | 22 | 22 | 22 | 28 | 43 | 23 | 22 | 29 |
| Surface smoothness (%) | 85 | 88 | 99 | 53 | 90 | 5 | 66 | 15 |
| Surface roughness (nm) | <10 | <10 | <10 | <10 | 200 | 100 | <10 | 100 |
| Non-sphericity (%) | 0.9 | 0.9 | 0.9 | 1.2 | 18.0 | 1.0 | 1.0 | 1.0 |
| Specific surface area ($m^2/g$) | 98 | 98 | 98 | 99 | 97 | 99 | 98 | 98 |
| Oil absorption rate (ml/100 g) | 24 | 24 | 24 | 24 | 24 | 24 | 24 | 24 |
| Pore volume (ml/g) | 0.1 | 0.1 | 0.1 | 0.1 | 0.1 | 0.1 | 0.1 | 0.1 |
| Compressive strength ($Kgf/mm^2$) | 48 | 48 | 48 | 49 | 48 | 49 | 49 | 49 |
| Silica purity (wt %) | 99.2 | 99.2 | 99.2 | 99.2 | 99.2 | 99.2 | 99.2 | 99.2 |
| Drying loss (wt %) | 0.1 | 0.1 | 0.1 | 0.1 | 0.1 | 0.2 | 0.1 | 0.1 |
| Ignition loss (wt %) | 2.0 | 2.0 | 2.0 | 2.0 | 2.0 | 2.0 | 2.0 | 2.0 |

TABLE 7

|  | Example No. | | | Comparative Example No. | | | | |
| --- | --- | --- | --- | --- | --- | --- | --- | --- |
|  | 8 | 9 | 10 | 1 | 2 | 3 | 4 | 5 |
| Prepared Calcined Powder | 3H | 3I | 3J | 3a | 3b | 3c | 3d | 3e |
| Average particle diameter (μm) | 5 | 5 | 5 | 5 | 5 | 5 | 5 | 5 |
| Coefficient of variation of particles (%) | 22 | 22 | 22 | 28 | 43 | 23 | 22 | 29 |
| Surface smoothness (%) | 85 | 89 | 100 | 53 | 90 | 5 | 66 | 15 |
| Surface roughness (nm) | <10 | <10 | <10 | <10 | 200 | 100 | <10 | 100 |
| Non-sphericity (%) | 0.9 | 0.9 | 0.9 | 1.1 | 16.9 | 1.1 | 0.9 | 1.1 |
| Specific surface area ($m^2/g$) | 101 | 101 | 101 | 101 | 100 | 101 | 100 | 100 |
| Oil absorption rate (ml/100 g) | 25 | 25 | 25 | 25 | 25 | 25 | 25 | 25 |
| Pore volume (ml/g) | 0.1 | 0.1 | 0.1 | 0.1 | 0.1 | 0.1 | 0.1 | 0.1 |
| Compressive strength ($Kgf/mm^2$) | 50 | 50 | 50 | 50 | 50 | 50 | 50 | 50 |
| Silica purity (wt %) | 99.2 | 99.2 | 99.2 | 99.2 | 99.2 | 99.2 | 99.2 | 99.2 |
| Drying loss (wt %) | 0.1 | 0.1 | 0.1 | 0.1 | 0.1 | 0.1 | 0.1 | 0.1 |
| Ignition loss (wt %) | 0.4 | 0.4 | 0.4 | 0.4 | 0.4 | 0.4 | 0.4 | 0.4 |

Comparative Example 6

Dried Powder 1A of porous silica-based particles obtained in the step (a) in Example 1 was classified using a separator-type dry classification device (TTSP, manufactured by Hosokawa Micron Corporation) under such conditions that particles having particle diameters of more than 15 μm were separated. Thus, a dried powder of porous silica-based particles classified under a dry condition (hereinafter referred to as "Comparative Dried Powder 1f") was obtained.

For Comparative Dried Powder 1f thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 8.

Next, 2160 cc of pure water was added to 240 g of Comparative Calcined Powder 1f, and the mixture was adjusted to pH 8 by the addition of aqueous ammonia and was then stirred at a rotating speed of 140 rpm for one hour to prepare a dispersion having a solid content of 10% by weight. The zeta potential of particles contained in the dispersion was measured and found to be −35 mV.

The dispersion was subjected to the steps (c) to (f) described in Example 1, and the operation as described in Example 1 was performed to obtain Dried Powder 2f of porous silica-based particles (hereinafter referred to as "Comparative Dried Powder 2f").

For Comparative Dried Powder 2f thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 9.

Further, for Comparative Dried Powder 2f, the state of the surface of particles was observed by a scanning electron microscope with magnifying powers of 3,000 and 10,000. As a result, for both the magnifying powers, foreign matters such as small particles attached to the particle surface were seen.

Next, Comparative Dried Powder 2f thus obtained was calcined under the same conditions as in Example 1 to obtain Calcined Powder 3f of porous silica-based particles (hereinafter referred to as "Comparative Calcined Powder 3f").

For Comparative Calcined Powder 3f thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 10.

Figure 5:
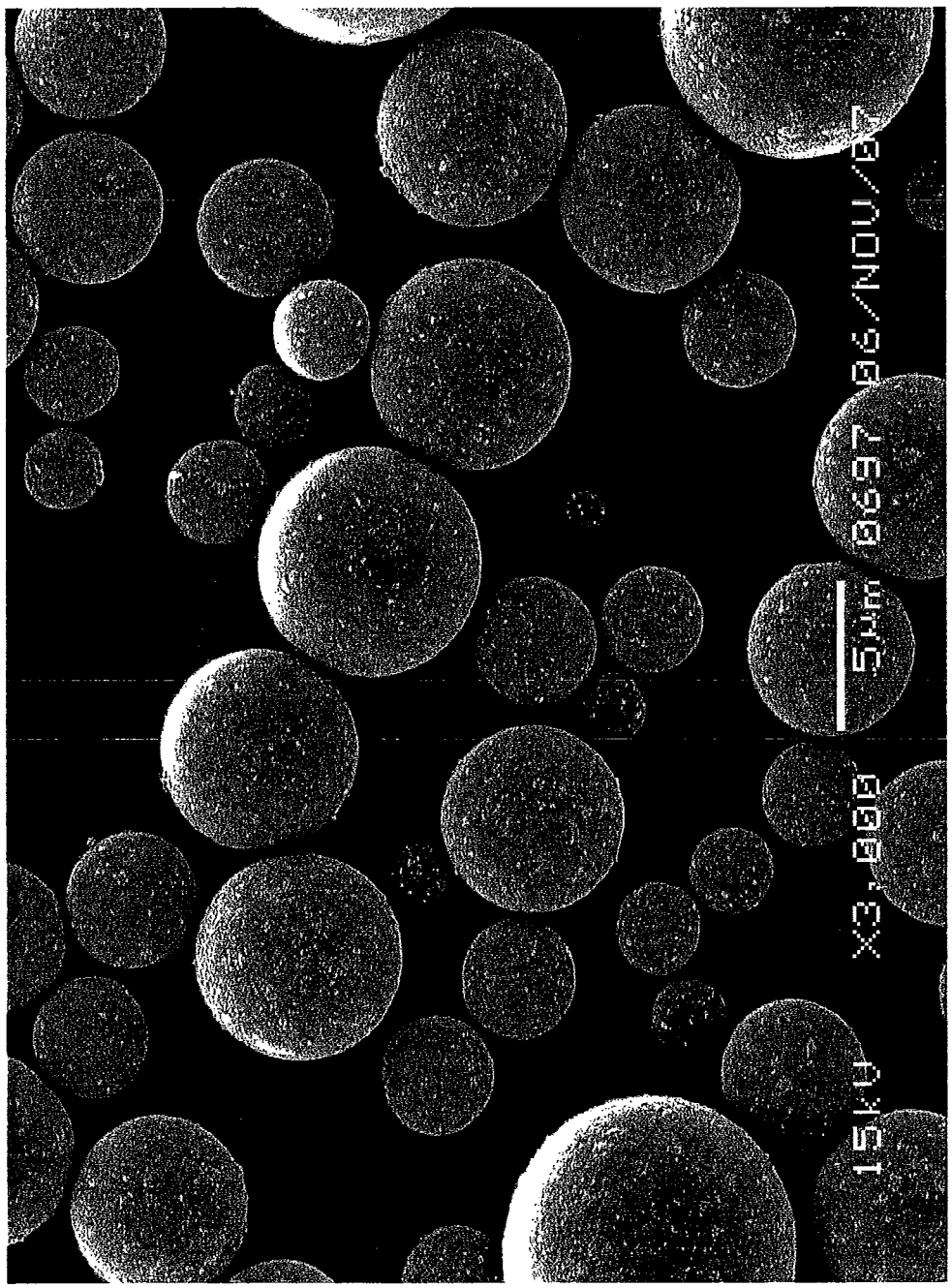
FIG. 5 is a photograph of porous silica-based particles, which were obtained in a calcination step in Comparative Example 6 (i.e., the particles produced by calcining a dried powder of porous silica-based particles classified under a dry condition), taken by a scanning electron microscope (SEM) with a magnifying power of 3,000.

Further, for Comparative Calcined Powder 3f, the state of the surface of particles was observed by a scanning electron microscope with magnifying powers of 3,000 and 10,000. As a result, for both the magnifying powers, foreign matters such as small particles attached to the particle surface were seen. In a photograph taken with a magnifying power of 10,000, attached matters other than small particles (the matters of which are attached as foreign matters produced on the particle surface as a result of collision against the side wall of the apparatus or abrasion of the particles) were seen. Photographs taken by an electron microscope (SEM) at that time are shown in FIG. 5 (magnifying power: 3,000) and FIG. 6 (magnifying power: 10,000).

Figure 12:
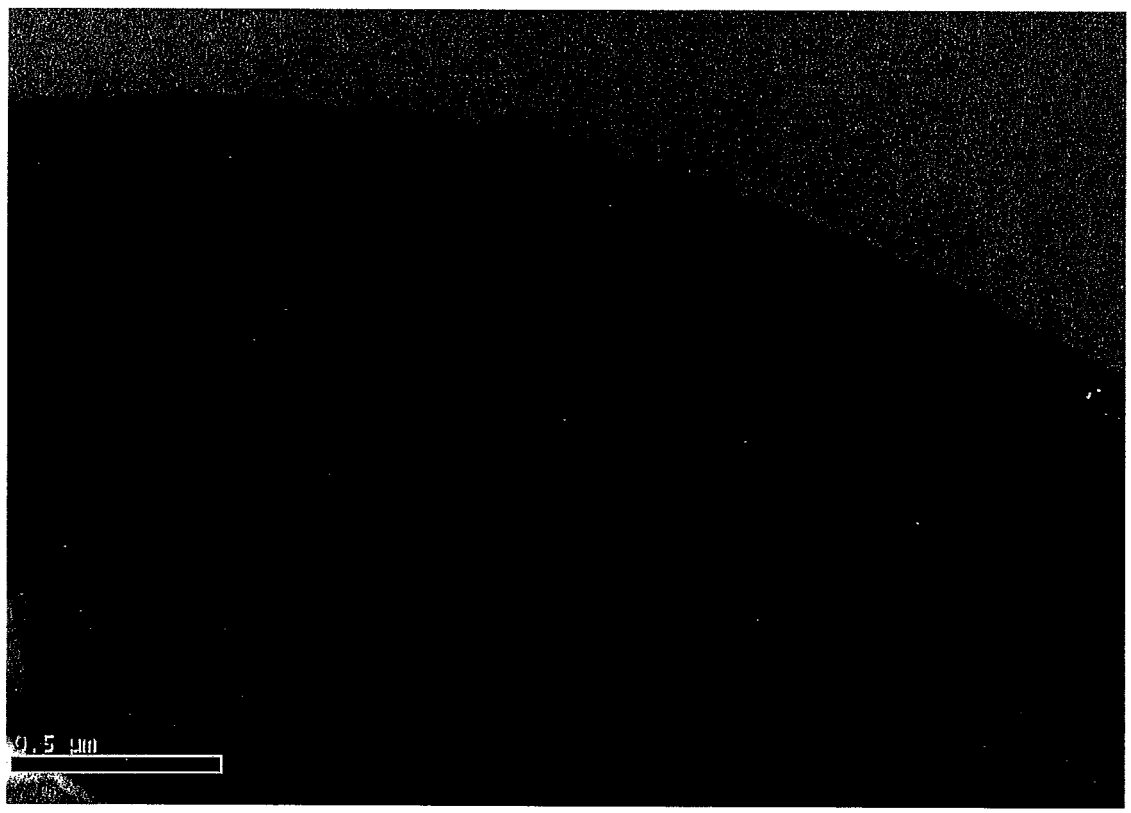
FIG. 12 is a photograph of cross-section of a porous silica-based particle, which was obtained in a calcination step in Comparative Example 6 (i.e., the particle produced by calcining a dried powder of porous silica-based particles classified under a dry condition), taken by a transmission electron microscope (TEM) with a magnifying power of 100,000.

When the cross-section of a particle of the calcined powder of the porous silica-based particles was observed by a transmission electron microscope with a magnifying power of 100,000, foreign matters such as small particles could be seen at a boundary of the particle. Further, a surface roughness value defined by a difference between a circumscribed circle and an inscribed circle of the particle was determined from a photograph taken at that time by an electron microscope (TEM) and was found to be 130 nm. The photograph taken by the electron microscope (TEM) is shown in FIG. 12.

Comparative Example 7

For a commercially available Calcined Powder 1h of porous silica-based particles (Silica micro bead P-1500, manufactured by JGC Catalysts and Chemicals Ltd.), the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 8.

2,160 cc of pure water was added to 240 g of Comparative Calcined Powder 1h, and the mixture was adjusted to pH 8 by the addition of aqueous ammonia and was stirred at a rotating speed of 140 rpm for one hour to prepare a dispersion having a solid content of 10% by weight. The zeta potential of particles contained in the dispersion was measured and found to be −35 my.

The dispersion was then subjected to the steps (c) to (f) described in Example 1, and the operation as described in Example 1 was performed to obtain Dried Powder 2h of pre-calcined porous silica-based particles (hereinafter referred to as "Comparative Dried Powder 2h").

For Comparative Dried Powder 2h thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 9.

Next, Comparative Dried Powder 2h thus obtained was calcined under the same conditions as in Example 1 to obtain Calcined Powder 3h of porous silica-based particles (hereinafter referred to as "Comparative Calcined Powder 3h").

For Comparative Calcined Powder 3h thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 10.

Figure 7:
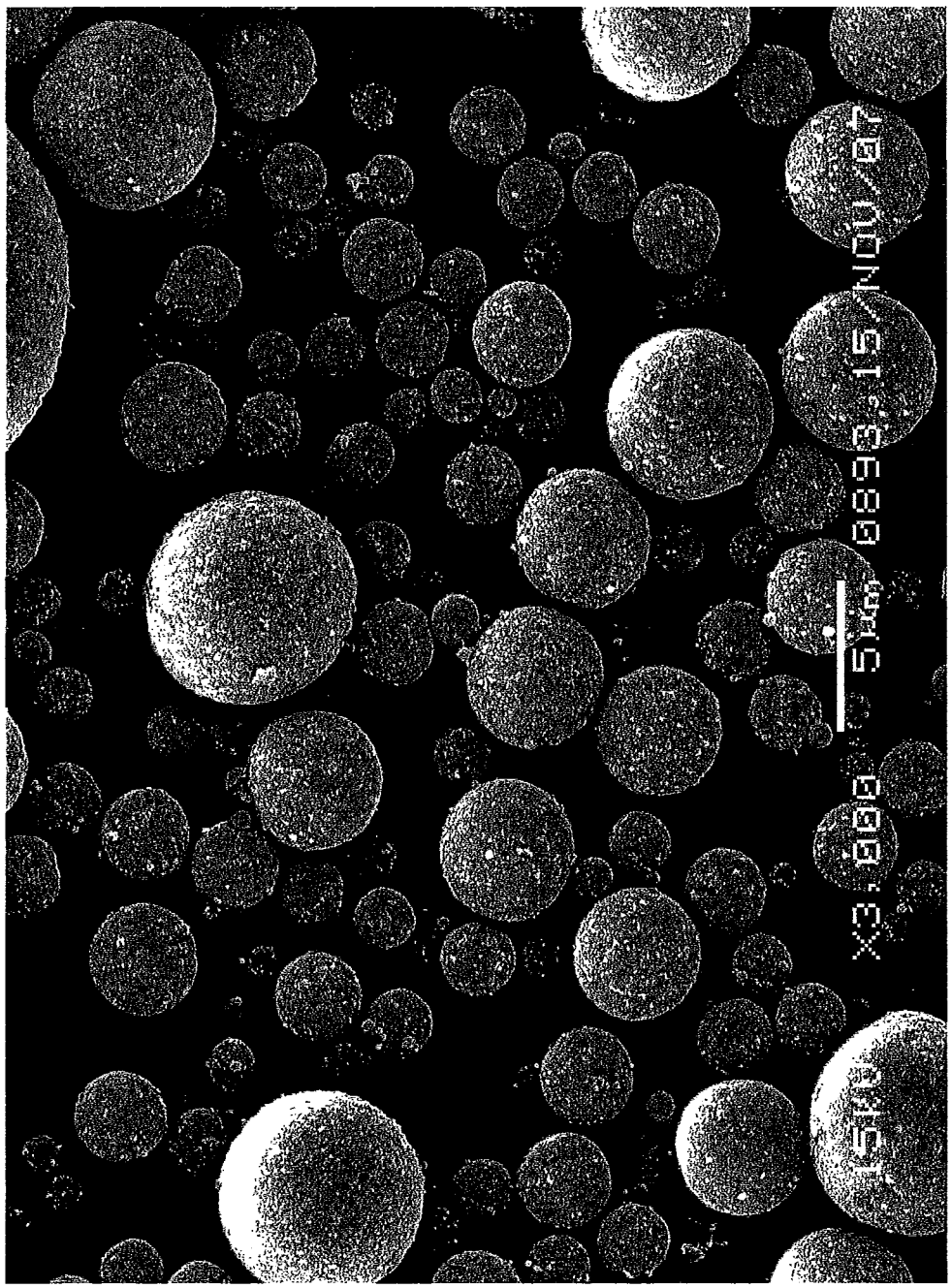
FIG. 7 is a photograph of porous silica-based particles, which were obtained in a calcination step in Comparative Example 7 (i.e., the particles produced by calcining a dried powder of commercially available calcined porous silica-based particles again), taken by a scanning electron microscope (SEM) with a magnifying power of 3,000.

Further, for Comparative Calcined Powder 3h, the state of the surface of particles was observed by a scanning electron microscope with magnifying powers of 3,000 and 10,000. As a result, as with Comparative Calcined Powder 3f obtained in Comparative Example 6, for both the magnifying powers, foreign matters such as small particles attached to the particle surface were seen. In a photograph taken with a magnifying power of 10,000, attached matters other than small particles (the matters of which are attached as foreign matters produced on the particle surface as a result of collision against the side wall of the apparatus or abrasion of the particles) were seen. Photographs taken by an electron microscope (SEM) at that time are shown in FIG. 7 (magnifying power: 3,000) and FIG. 8 (magnifying power: 10,000).

Comparative Example 8

2,160 cc of pure water was added to 240 g of commercially available Calcined Powder 1h of porous silica-based particles (Silica micro bead P-1500, manufactured by JGC Catalysts and Chemicals Ltd.) used in Comparative Example 7. The mixture was subjected to an ultrasonic cleaning device (US-3, 38 kHz, manufactured by SND CO., LTD.) and treated for 10 minutes to disperse the porous silica-based particles in the water and also to wash the surface of the particles, and thus, a dispersion having a solid content of 10% by weight was prepared. (However, this treatment was carried out in six divided portions because an ultrasonic cleaning device with a small capacity was used, and thereafter, such six divided portions of the dispersion were mixed.) The zeta potential of the particles contained in the dispersion was measured and found to be −33 mV.

The dispersion was then subjected to the step (c) described in Example 1, and the operation was performed under the same conditions as in Example 1, except that the operation was repeated six times.

Then, 600 cc of pure water was mixed with the sediment or precipitate (including a residual liquid), and the mixture was stirred for one hour.

Further, the mixture was subjected to the steps (d) to (f) described in Example 1, and the operation was performed under the same conditions as in Example 1 to obtain Dried Powder 2i of pre-calcined porous silica-based particles (hereinafter referred to as "Comparative Dried Powder 2i").

For Comparative Dried Powder 2i thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 9.

Next, Comparative Dried Powder 2i thus obtained was calcined under the same conditions as in Example 1 to obtain Calcined Powder 3i of porous silica-based particles (hereinafter referred to as "Comparative Calcined Powder 3i").

For Comparative Calcined Powder 3i thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 10.

Figure 9:
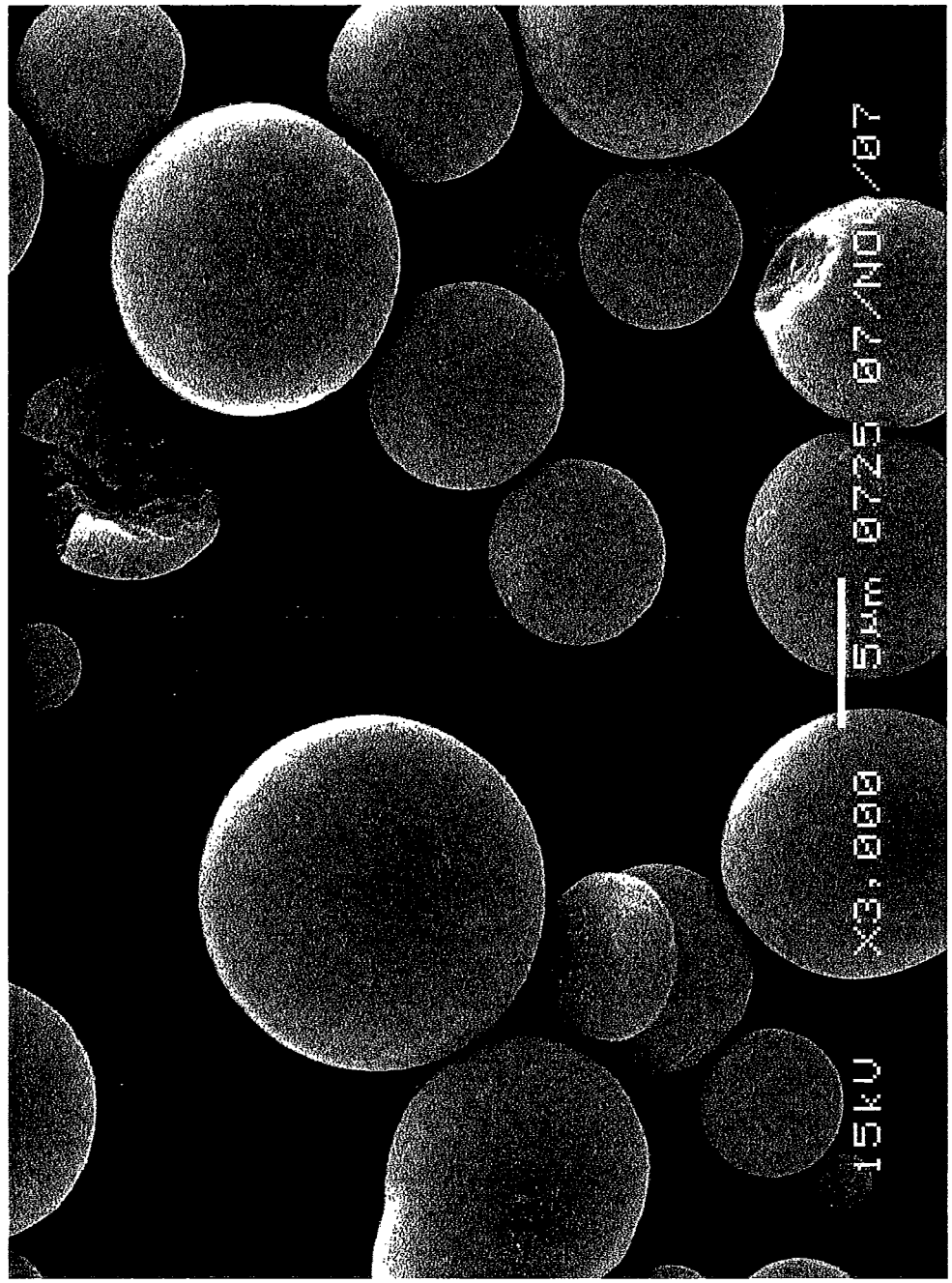
FIG. 9 is a photograph of porous silica-based particles, which were obtained in a calcination step in Comparative Example 8 (i.e., the particles produced by treating a calcined powder of porous silica-based particles with an ultrasonic cleaning device), taken by a scanning electron microscope (SEM) with a magnifying power of 3,000.

Further, for Comparative Calcined Powder 3i, the state of the surface of particles was observed by a scanning electron microscope with magnifying powers of 3,000 and 10,000. As a result, for both the magnifying powers, foreign matters such as small particles attached to the particle surface were seen, although the degree of attachment of the foreign matter is not so significant as compared with that in Comparative Calcined Powder 3f obtained in Comparative Example 6. Further, some non-spherical particles produced as a result of cracking of spherical particles were seen. Further, in a photograph taken with a magnifying power of 10,000, the attachment of foreign matters other than small particles on the particle surface was seen. Photographs taken by an electron microscope (SEM) at that time are shown in FIG. 9 (magnifying power: 3,000) and FIG. 10 (magnifying power: 10,000).

Comparative Example 9

2,160 cc of pure water was added to 240 g of the dried powder of porous silica-based particles obtained in Comparative Example 6, that is, 240 g of Comparative Dried Powder if classified under a dry condition. The mixture was subjected to an ultrasonic cleaning device (US-3, 38 kHz, manufactured by SND CO., LTD.) and treated for 10 minutes to disperse the porous silica-based particles in the water and also to wash the surface of the particles, and thus, a dispersion having a solid content of 10% by weight was prepared. (However, this treatment was carried out in six divided portions because an ultrasonic cleaning device with a small capacity was used, and thereafter, such six divided portions of the dispersion were mixed.) The zeta potential of the particles contained in the dispersion was measured and found to be −33 mV.

The dispersion was then subjected to the steps (c) to (f) described in Comparative Example 8, and the operation was performed under the same conditions as in Comparative Example 8 to obtain Dried Powder 2j of porous silica-based particles (hereinafter referred to as "Comparative Dried Powder 2j").

For Comparative Dried Powder 2j thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 9.

Next, Comparative Dried Powder 2j thus obtained was calcined under the same conditions as in Example 1 to obtain Calcined Powder 3j of porous silica-based particles (hereinafter referred to as "Comparative Calcined Powder 3j").

For Comparative Calcined Powder 3j thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 10.

Further, for Comparative Calcined Powder 3j, the state of the surface of particles was observed by a scanning electron microscope with magnifying powers of 3,000 and 10,000. As a result, for both the magnifying powers, foreign matters such as small particles attached to the particle surface were not seen. However, a number of non-spherical particles produced as a result of cracking of spherical particles were seen.

Comparative Example 10

The supernatant containing porous silica-based particles mainly having particle diameters of not more than 0.5 μm, which had been separated and removed in the step (c) in Example 4, was subjected to the steps (e) and (f) described in Example 1, and the operation was performed under the same conditions as in Example 1 to obtain Dried Powder 2k of porous silica-based particles (hereinafter referred to as "Comparative Dried Powder 2k").

For Comparative Dried Powder 2k thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 9.

Further, for Comparative Dried Powder 2k, the state of the surface of particles was observed by a scanning electron microscope with magnifying powers of 3,000 and 10,000. As a result, for both the magnifying powers, foreign matters such as small particles attached to the particle surface could be hardly seen.

Next, Comparative Dried Powder 2k thus obtained was calcined under the same conditions as in Example 1 to obtain Calcined Powder 3k of porous silica-based particles (hereinafter referred to as "Comparative Calcined Powder 3k").

For Comparative Calcined Powder 3k thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 10.

Further, for Comparative Calcined Powder 3k, the state of the surface of particles was observed by a scanning electron microscope with magnifying powers of 3,000 and 10,000. As a result, for both the magnifying powers, foreign matters such as small particles attached to the particle surface could be hardly seen. The average particle diameter of Comparative Calcined Powder 2k thus obtained, however, was 0.3 μm.

Comparative Calcined Powder 2k was prepared for use in Comparative Examples which will be described later.

Comparative Example 11

The sediment or precipitate (including a residual liquid) containing porous silica-based particles mainly having particle diameters of not less than 30 μm which had been separated and removed in the step (d) in Example 3, was subjected to the steps (e) and (f) described in Example 1, and the operation was performed under the same conditions as in Example 1 to obtain Dried Powder 2n of porous silica-based particles (hereinafter referred to as "Comparative Dried Powder 2n").

For Comparative Dried Powder 2n thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 9.

Further, for Comparative Dried Powder 2n, the state of the surface of particles was observed by a scanning electron microscope with magnifying powers of 3,000 and 10,000. As a result, for both the magnifying powers, foreign matters such as small particles attached to the particle surface could be hardly seen.

Next, Comparative Dried Powder 2n thus obtained was calcined under the same conditions as in Example 1 to obtain Calcined Powder 3n of porous silica-based particles (hereinafter referred to as "Comparative Calcined Powder 3n").

For Comparative Calcined Powder 3n thus obtained, the average particle diameter, coefficient of variation of particles, surface smoothness, surface roughness, non-sphericity, specific surface area, oil absorption rate, pore volume, compressive strength, silica purity, drying loss, and ignition loss were determined in the same manner as in Example 1. The results are shown in Table 10.

Further, for Comparative Calcined Powder 3n, the state of the surface of particles was observed by a scanning electron microscope with magnifying powers of 3,000 and 10,000. As a result, for both the magnifying powers, foreign matters such as small particles attached to the particle surface could be hardly seen. The average particle diameter of Comparative Calcined Powder 2n, however, was 34 μm.

Comparative Calcined Powder 2n was prepared for use in Comparative Examples which will be described later.

TABLE 8

| | Comparative Example No. | |
|---|---|---|
| | 6 | 7 |
| Dried powder or calcined powder used | Comparative Dried Powder 1f (dry-classified product) | Comparative Calcined Powder 1h (commercially available product) |
| Average particle diameter (μm) | 5 | 5 |
| Coefficient of variation of particles (%) | 59 | 58 |
| Surface smoothness (%) | 0 | 0 |
| Non-sphericity (%) | 4.1 | 2.3 |
| Specific surface area (m$^2$/g) | 143 | 150 |
| Pore volume (ml/g) | 0.3 | 0.3 |
| Drying loss (wt %) | 4 | 0.1 |
| Ignition loss (wt %) | 7 | 1.4 |

TABLE 9

| | Comparative Example No. | | | | | |
|---|---|---|---|---|---|---|
| | 6 | 7 | 8 | 9 | 10 | 11 |
| Comparative Dried Powder | 2f | 2h | 2i | 2j | 2k | 2n |
| Average particle diameter (μm) | 5 | 5 | 5 | 4 | 0.3 | 34 |
| Coefficient of variation of particles (%) | 28 | 30 | 46 | 52 | 22 | 55 |
| Surface smoothness (%) | 0 | 0 | 28 | 71 | 100 | 99 |
| Surface roughness (nm) | 130 | 250 | 160 | <10 | <10 | <10 |
| Non-sphericity (%) | 1.8 | 1.4 | 6.5 | 28.2 | 1.1 | 4.3 |
| Specific surface area (m$^2$/g) | 143 | 143 | 143 | 143 | 143 | 143 |
| Oil absorption rate (ml/100 g) | 57 | 57 | 57 | 57 | 57 | 57 |
| Pore volume (ml/g) | 0.3 | 0.3 | 0.3 | 0.3 | 0.3 | 0.3 |
| Compressive strength (Kgf/mm$^2$) | 8 | 10 | 10 | 8 | <0.1 | 6 |
| Silica purity (wt %) | 99.3 | 99.3 | 99.3 | 99.3 | 99.3 | 99.3 |
| Drying loss (wt %) | 0.1 | 0.1 | 0.1 | 0.1 | 0.1 | 0.1 |
| Ignition loss (wt %) | 2.8 | 2.8 | 2.8 | 2.8 | 2.6 | 2.8 |

TABLE 10

| | Comparative Example No. | | | | | |
|---|---|---|---|---|---|---|
| | 6 | 7 | 8 | 9 | 10 | 11 |
| Comparative Calcined Powder | 3f | 3h | 3i | 3j | 3k | 3n |
| Average particle diameter (μm) | 5 | 5 | 5 | 4 | 0.3 | 34 |
| Coefficient of variation of particles (%) | 28 | 30 | 46 | 52 | 22 | 55 |
| Surface smoothness (%) | 0 | 0 | 27 | 70 | 100 | 99 |
| Surface roughness (nm) | 130 | 250 | 160 | <10 | <10 | <10 |
| Non-sphericity (%) | 1.7 | 1.4 | 6.3 | 28.2 | 1.1 | 4.3 |

TABLE 10-continued

|  | Comparative Example No. | | | | | |
|---|---|---|---|---|---|---|
|  | 6 | 7 | 8 | 9 | 10 | 11 |
| Specific surface area (m$^2$/g) | 150 | 150 | 150 | 150 | 150 | 150 |
| Oil absorption rate (ml/100 g) | 60 | 60 | 60 | 60 | 60 | 60 |
| Pore volume (ml/g) | 0.3 | 0.3 | 0.3 | 0.3 | 0.3 | 0.3 |
| Compressive strength (Kgf/mm$^2$) | 10 | 10 | 10 | 10 | <0.1 | 7 |
| Silica purity (wt %) | 99.3 | 99.3 | 99.3 | 99.3 | 99.3 | 99.3 |
| Drying loss (wt %) | 0.1 | 0.1 | 0.1 | 0.1 | 0.1 | 0.1 |
| Ignition loss (wt %) | 1.3 | 1.0 | 1.1 | 1.3 | 1.4 | 1.2 |

Example 11 and Comparative Example 12

Sensory Test of the Calcined Powders

Example Calcined Powders 3A to 3J obtained in Examples 1 to 10 and Comparative Calcined Powders 3a to 3n (except for 3g, 3l, and 3m that were unused numbers) obtained in Comparative Examples 1 to 11 were provided, and feeling properties upon applying these powders onto the skin were evaluated by the expert panelists in accordance with the above test method. The results are shown in Table 11.

As a result, it was found that the Example Calcined Powders were excellent and suitable as a feeling-improving material for cosmetics, whereas the Comparative Calcined Powders were unsuitable as the feeling-improving material.

TABLE 11

| Evaluation Samples | Feeling A | Feeling B | Feeling C | Feeling D | Feeling E | Feeling F | Feeling G |
|---|---|---|---|---|---|---|---|
| Example Calcined Powder 3A | ◎ | ◎ | ◎ | ◎ | ◎ | ◎ | ◎ |
| Example Calcined Powder 3B | ◎ | ◎ | ◎ | ◎ | ◎ | ◎ | ◎ |
| Example Calcined Powder 3C | ◎ | ○ | ○ | ○ | ○ | ◎ | △ |
| Example Calcined Powder 3D | △ | ◎ | △ | ○ | ◎ | △ | ◎ |
| Example Calcined Powder 3E | ○ | ◎ | ○ | ○ | ◎ | ○ | ◎ |
| Example Calcined Powder 3F | ◎ | ○ | ○ | ○ | ○ | ○ | ○ |
| Example Calcined Powder 3G | ◎ | ○ | ◎ | ◎ | ○ | ○ | ◎ |
| Example Calcined Powder 3H | ○ | ○ | ○ | ○ | ○ | ○ | ◎ |
| Example Calcined Powder 3I | ○ | ○ | ○ | ○ | ◎ | ○ | ◎ |
| Example Calcined Powder 3J | ○ | ◎ | ○ | ○ | ◎ | ○ | ◎ |
| Comparative Calcined Powder 3a | △ | ○ | △ | ○ | ○ | △ | ○ |
| Comparative Calcined Powder 3b | △ | ○ | ○ | ▲ | ○ | X | ○ |
| Comparative Calcined Powder 3c | △ | ○ | X | ○ | ○ | △ | △ |
| Comparative Calcined Powder 3d | △ | ○ | ○ | ○ | ○ | △ | ○ |
| Comparative Calcined Powder 3e | △ | ○ | ▲ | ○ | ○ | △ | △ |
| Comparative Calcined Powder 3f | ▲ | ○ | ○ | ▲ | ○ | ▲ | ○ |
| Comparative Calcined Powder 3h | ▲ | ▲ | △ | △ | ○ | △ | ○ |
| Comparative Calcined Powder 3i | ▲ | △ | △ | ▲ | ○ | △ | △ |
| Comparative Calcined Powder 3j | X | △ | ▲ | X | ▲ | ▲ | ○ |
| Comparative Calcined Powder 3k | X | ○ | X | X | ○ | X | ◎ |
| Comparative Calcined Powder 3n | ○ | ▲ | △ | ▲ | ▲ | ○ | X |

(Note)
Feeling A: Smoothness
Feeling B: Moistness
Feeling C: Rolling Effect
Feeling D: Even Spreadability
Feeling E: Adhesiveness to the Skin
Feeling F: Sustainability of the Rolling Effect
Feeling G: Little Grating Example 12 and Comparative Example 13

Preparation of Powder Foundation

Each of the ingredient (1) selected from Example Calcined Powders 3A to 3J obtained in Examples 1 to 10 and Comparative Calcined Powders 3a to 3n (except for 3g, 3l, and 3m that were unused numbers) obtained in Comparative Examples 1 to 11, and Ingredients (2) to (9) as shown in Table 12 were put into a mixer at a blending ratio (% by weight) of Table 12, and the mixture was then stirred for homogeneous mixing. Next, Ingredients (10) to (12) as shown in Table 12 were put into the mixer and the mixture was then stirred for homogeneous mixing. Then, each of the cake-like substances thus obtained was broken up, and about 12 g of each was extracted from the substances and was placed in a square gold dish having a size of 46 mm×54 mm×4 mm, followed by pressing.

Thus, Example Cosmetics A to J in which Example Calcined Powders 3A to 3J were blended, and Comparative Cosmetics a to n in which Comparative Calcined Powders 3a to 3n (except for 3g, 3l, and 3m that were unused numbers) were blended, were obtained.

TABLE 12

| | Ingredients of cosmetic constituting powder foundation | Blending amount (wt %) |
|---|---|---|
| (1) | Each powder selected from Example Calcined Powders 3A to 3M and Comparative Calcined Powders 3a to 3n | 10.0 |
| (2) | Sericite (treated with silicon) | 40.0 |
| (3) | Talc (treated with silicon) | 29.0 |
| (4) | Mica (treated with silicon) | 5.0 |
| (5) | Titanium oxide (treated with silicon) | 7.0 |
| (6) | Yellow iron oxide (treated with silicon) | 1.2 |
| (7) | Red iron oxide (treated with silicon) | 0.4 |

TABLE 12-continued

| | Ingredients of cosmetic constituting powder foundation | Blending amount (wt %) |
|---|---|---|
| (8) | Black iron oxide (treated with silicon) | 0.2 |
| (9) | Methyl paraben | 0.2 |
| (10) | Dimethicone | 4.0 |
| (11) | Liquid paraffin | 2.0 |
| (12) | Glyceryl tri-2-ethylhexanoate | 1.0 |

Next, by using the powder foundation each selected from Example Cosmetics A to J and Comparative Cosmetics a to n thus obtained, feeling properties upon applying it onto the skin and also after having applied thereon were evaluated by the expert panelists in accordance with the above test method. The results are shown in Table 13.

As a result, it was found that the Example Cosmetics were excellent in feeling properties of use both upon applying them onto the skin and even after they have been applied onto the skin, whereas the Comparative Cosmetics had poor feelings of use.

TABLE 13

| | Upon Applying | | | After having been applied | | |
|---|---|---|---|---|---|---|
| Evaluation Samples | Feeling A | Feeling B | Feeling C | Feeling D | Feeling E | Feeling F |
| Example Cosmetic A | ⊚ | ○ | ⊚ | ⊚ | ○ | ⊚ |
| Example Cosmetic B | ⊚ | ○ | ⊚ | ⊚ | ○ | ⊚ |
| Example Cosmetic C | ⊚ | ○ | Δ | ○ | ○ | ○ |
| Example Cosmetic D | Δ | ○ | ○ | ○ | ○ | ⊚ |
| Example Cosmetic E | ⊚ | ⊚ | ⊚ | ⊚ | ⊚ | ⊚ |
| Example Cosmetic F | ⊚ | ○ | ⊚ | ⊚ | ○ | ○ |
| Example Cosmetic G | ⊚ | ○ | ⊚ | ⊚ | ○ | ○ |
| Example Cosmetic H | ○ | ○ | ○ | ○ | ○ | ○ |
| Example Cosmetic I | ⊚ | ○ | ⊚ | ⊚ | ○ | ⊚ |
| Example Cosmetic J | ⊚ | ⊚ | ⊚ | ⊚ | ⊚ | ⊚ |
| Comparative Cosmetic a | Δ | Δ | ○ | ○ | Δ | Δ |
| Comparative Cosmetic b | X | Δ | ○ | X | Δ | Δ |
| Comparative Cosmetic c | Δ | Δ | ○ | Δ | Δ | Δ |
| Comparative Cosmetic d | Δ | Δ | ○ | ○ | Δ | Δ |
| Comparative Cosmetic e | Δ | Δ | ○ | Δ | Δ | Δ |
| Comparative Cosmetic f | ▲ | Δ | ○ | ○ | Δ | Δ |
| Comparative Cosmetic h | ▲ | ▲ | Δ | ○ | ▲ | ▲ |
| Comparative Cosmetic i | ▲ | Δ | ▲ | Δ | Δ | ▲ |
| Comparative Cosmetic j | X | Δ | X | Δ | ○ | Δ |
| Comparative Cosmetic k | X | Δ | X | X | ○ | ▲ |
| Comparative Cosmetic n | ▲ | ▲ | X | ▲ | ▲ | ▲ |

(Note)
Feeling A: Even Spreadability
Feeling B: Moistness
Feeling C: Smoothness
Feeling D: Uniformity of the Cosmetic Film
Feeling E: Moistness of the Cosmetic Film
Feeling F: Softness of the Cosmetic Film

BRIEF DESCRIPTION OF THE DRAWINGS

FIG. 1 is a photograph of porous silica-based particles, which were obtained in step (a) (that is, a spray-drying step) in Example 1, taken by a scanning electron microscope (SEM) with a magnifying power of 3,000.

FIG. 2 is a photograph of porous silica-based particles, which were obtained in step (a) (that is, a spray-drying step) in Example 1, taken by a scanning electron microscope (SEM) with a magnifying power of 10,000.

FIG. 3 is a photograph of porous silica-based particles, which were obtained in a calcination step in Example 1 (i.e., the particles produced by calcining a dried powder of porous silica-based particles classified under a wet condition), taken by a scanning electron microscope (SEM) with a magnifying power of 3,000.

FIG. 4 is a photograph of porous silica-based particles, which were obtained in a calcination step in Example 1 (i.e., the particles produced by calcining a dried powder of porous silica-based particles classified under a wet condition), taken by a scanning electron microscope (SEM) with a magnifying power of 10,000.

FIG. 5 is a photograph of porous silica-based particles, which were obtained in a calcination step in Comparative Example 6 (i.e., the particles produced by calcining a dried powder of porous silica-based particles classified under a dry condition), taken by a scanning electron microscope (SEM) with a magnifying power of 3,000.

Figure 6:
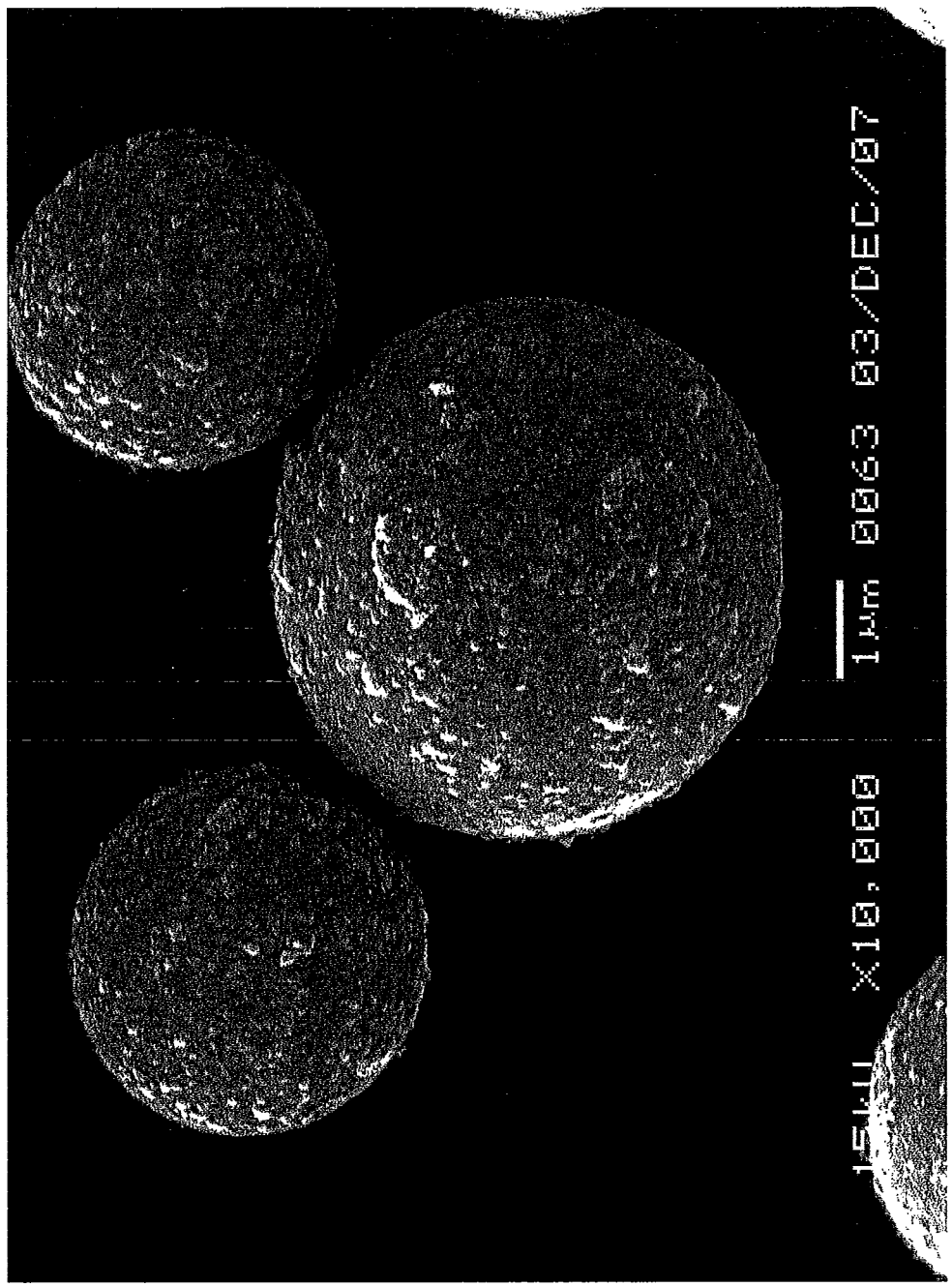
FIG. 6 is a photograph of porous silica-based particles, which were obtained in a calcination step in Comparative Example 6 (i.e., the particles produced by calcining a dried powder of porous silica-based particles classified under a dry condition), taken by a scanning electron microscope (SEM) with a magnifying power of 10,000.

FIG. 6 is a photograph of porous silica-based particles, which were obtained in a calcination step in Comparative Example 6 (i.e., the particles produced by calcining a dried powder of porous silica-based particles classified under a dry condition), taken by a scanning electron microscope (SEM) with a magnifying power of 10,000.

FIG. 7 is a photograph of porous silica-based particles, which were obtained in a calcination step in Comparative Example 7 (i.e., the particles produced by calcining a dried powder of commercially available calcined porous silica-based particles again), taken by a scanning electron microscope (SEM) with a magnifying power of 3,000.

Figure 8:
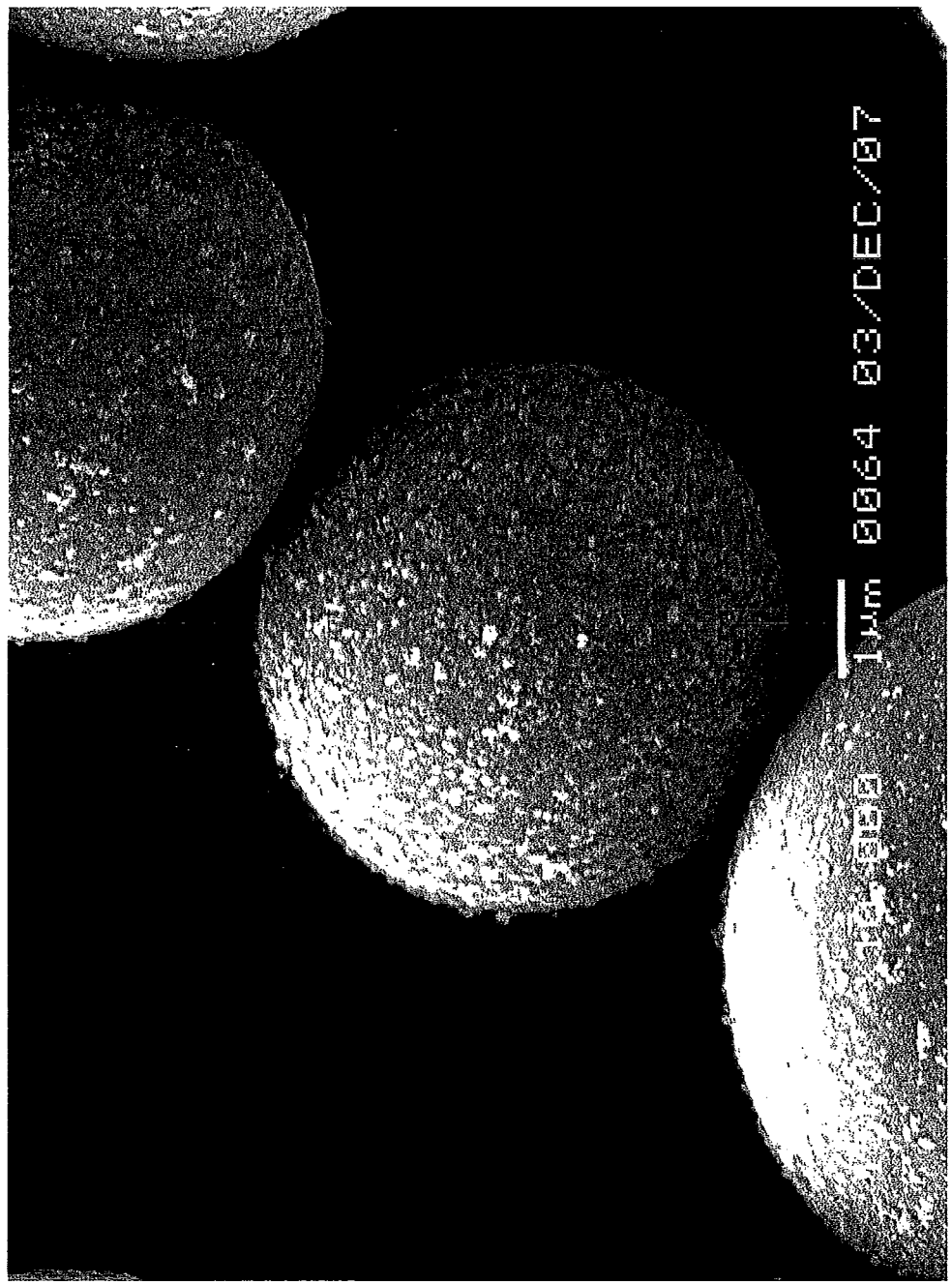
FIG. 8 is a photograph of porous silica-based particles, which were obtained in a calcination step in Comparative Example 7 (i.e., the particles produced by calcining a dried powder of commercially available calcined porous silica-based particles again), taken by a scanning electron microscope (SEM) with a magnifying power of 10,000.

FIG. 8 is a photograph of porous silica-based particles, which were obtained in a calcination step in Comparative Example 7 (i.e., the particles produced by calcining a dried powder of commercially available calcined porous silica-based particles again), taken by a scanning electron microscope (SEM) with a magnifying power of 10,000.

FIG. 9 is a photograph of porous silica-based particles, which were obtained in a calcination step in Comparative Example 8 (i.e., the particles produced by treating a calcined powder of porous silica-based particles with an ultrasonic cleaning device), taken by a scanning electron microscope (SEM) with a magnifying power of 3,000.

Figure 10:
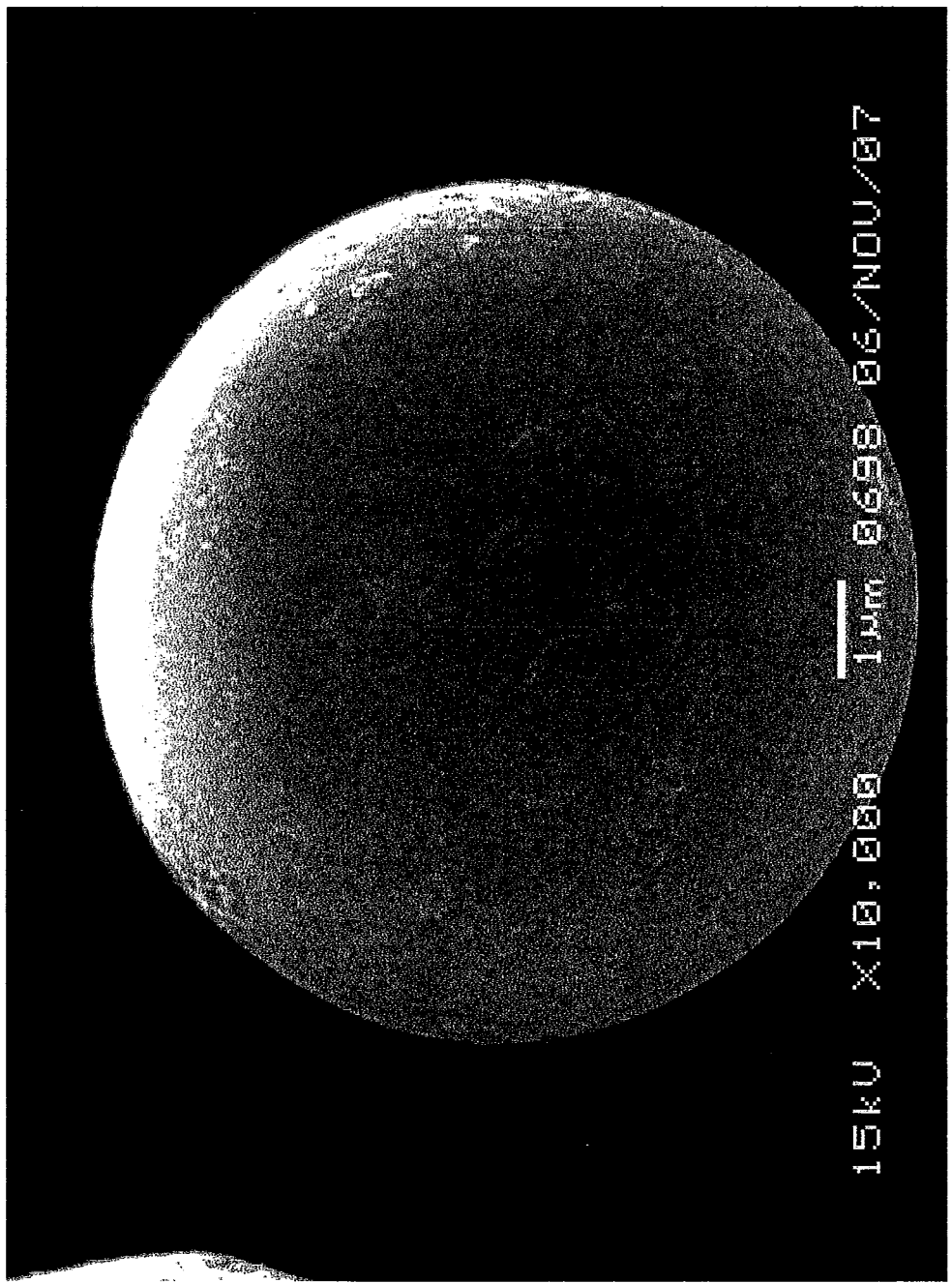
FIG. 10 is a photograph of porous silica-based particles, which were obtained in a calcination step in Comparative Example 8 (i.e., the particles produced by treating a calcined powder of porous silica-based particles with an ultrasonic cleaning device), taken by a scanning electron microscope (SEM) with a magnifying power of 10,000.

FIG. 10 is a photograph of porous silica-based particles, which were obtained in a calcination step in Comparative Example 8 (i.e., the particles produced by treating a calcined powder of porous silica-based particles with an ultrasonic cleaning device), taken by a scanning electron microscope (SEM) with a magnifying power of 10,000.

FIG. 11 is a photograph of cross-section of a porous silica-based particle, which was obtained in a calcination step in Example 1 (i.e., the particle produced by calcining a dried powder of porous silica-based particles classified under a wet condition), taken by a transmission electron microscope (TEM) with a magnifying power of 100,000.

FIG. 12 is a photograph of cross-section of a porous silica-based particle, which was obtained in a calcination step in Comparative Example 6 (i.e., the particle produced by calcining a dried powder of porous silica-based particles classified under a dry condition), taken by a transmission electron microscope (TEM) with a magnifying power of 100,000.

The invention claimed is:

1. Porous silica-based particles formed from a plurality of fine silica primary particles,
    wherein the primary particles are spherical or non-spherical having an average particle diameter of 0.005 to 0.1 µm,
    wherein the porous silica-based particles are formed from bonding of the primary particles, the porous silica-based particles having an average particle diameter of 0.5 to 30 µm and having a surface smoothness of a level to such an extent that, when the entire surface of the porous silica-based particle is observed from a photograph thereof taken by a scanning electron microscope (SEM) with a magnifying power of 10,000, the number of foreign matter attached to the surface of the porous silica-based particle including foreign particles observed as white dots on the photograph per µm$^2$ of the surface of the silica-based particle, is five or fewer, as determined by using the SEM photograph,
    wherein, when a surface roughness value of the porous silica-based particle is given by measuring a difference between a circumscribed circle and an inscribed circle at a boundary of the porous silica-based particle observed from a photograph of a cross-section thereof taken by a transmission electron microscope (TEM) with a magnifying power of 100,000, the porous silica-based particles have a surface roughness value of not more than 20 nm,
    the porous silica-based particles have an oil absorption rate in a range of 20 to 300 ml/100 g,
    the porous silica-based particles have a pore volume in a range of 0.05 to 3.0 ml/g,
    the porous silica-based particles have a coefficient of variation (CV value) in a range of 5% to 50%, and
    the specific surface area of the particle is 97 to 320 m$^2$/g.

2. The porous silica-based particles according to claim 1, wherein the porous silica-based particles have a non-sphericity of not more than 5%.

3. The porous silica-based particles according to claim 1, wherein the porous silica-based particles have a silica purity (SiO$_2$ content) of not less than 96% by weight.

4. A cosmetic comprising the porous silica-based particles having a surface smoothness according to claim 1.

5. The cosmetic according to claim 4, wherein the cosmetic is a makeup cosmetic, a skin care cosmetic, or a sunscreen cosmetic.

6. A method for producing the porous silica-based particles of claim 1, having an average particle diameter of 0.5 to 30 µm and having a surface smoothness of a level to such an extent that, when the entire surface of the particle is observed from a photograph thereof taken by a scanning electron microscope (SEM) with a magnifying power of 10,000, a foreign matter attached to the surface thereof can be hardly seen, which comprises the steps of:
    (a) spray-drying a dispersion of fine silica-based particles, or a mixture of the above dispersion of the fine silica-based particles and an aqueous solution of silicic acid with use of a spray dryer, to obtain a dried powder of porous silica-based particles having diameters ranging primarily from 0.1 to 50 µm;
    (b) putting the dried powder of the porous silica-based particles obtained in the step (a) into water and then stirring a slurry of the mixture under pH conditions on which the zeta potential of the porous silica-based particles contained in the water comes to in a range of −15 to −70 mV, to obtain a dispersion of porous silica-based particles with a foreign matter attached to the surface thereof having been removed therefrom;
    (c) subjecting the dispersion obtained in the step (b) to a wet classification device at which a supernatant containing at least porous silica-based particles having diameters of less than 0.5 µm is separated and removed, to obtain a dispersion containing porous silica-based particles having diameters ranging primarily from 0.5 to 50 µm;
    (d) subjecting the dispersion obtained in the step (c) to a wet classification device at which a sediment or precipitates containing at least porous silica-based particles having diameters of more than 30 µm is separated and removed, to obtain a dispersion containing porous silica-based particles having diameters ranging primarily from 0.5 to 30 μm;

(e) filtering the dispersion obtained in the step (d) to separate solid materials contained therein, to obtain a cake-like substance of porous silica-based particles; and (f) drying the cake-like substance obtained in the step (e) and then crushing or breaking up a group of thus obtained particles, to obtain a dried powder of porous silica-based particles having an average particle diameter of 0.5 to 30 μm.

7. The method for producing porous silica-based particles according to claim 6, wherein, in the step (b) above, the pH of the slurry containing the dried powder of the porous silica-based particles is in a range of 5 to 10.

8. The method for producing porous silica-based particles according to claim 6, wherein, in the step (b) above, the zeta potential of the porous silica-based particles contained in the water is in a range of −20 to −60 mV.

9. The method for producing porous silica-based particles according to claim 6, wherein the stirring operation in the step (b) above is performed for at least three minutes at a stirring speed of 10 to 5000 rpm.

10. The method for producing porous silica-based particles according to claim 6, wherein the wet classification device used in the step (c) above is a centrifugal separator, a liquid cyclone, or an elutriator (a natural sedimentation device).

11. The method for producing porous silica-based particles according to claim 6, wherein the wet classification device used in the step (d) above is a centrifugal separator, a liquid cyclone, or an elutriator (a natural sedimentation device).

12. The method for producing porous silica-based particles according to claim 6, wherein the drying operation in the step (f) above is performed for 1 to 24 hours at a temperature of room temperature to 200° C.

13. The method for producing porous silica-based particles according to claim 6, wherein the dried powder of the porous silica-based particles obtained in the step (f) above is further calcined at a temperature of 200 to 800° C. for 1 to 24 hours.

* * * * *